US010363260B2

(12) United States Patent
Berenson

(10) Patent No.: US 10,363,260 B2
(45) Date of Patent: Jul. 30, 2019

(54) ANTI-CANCER EFFECTS OF JAK2 INHIBITORS IN COMBINATION WITH THALIDOMIDE DERIVATIVES AND GLUCOCORTICOIDS

(71) Applicant: Institute for Myeloma & Bone Cancer Research, West Hollywood, CA (US)

(72) Inventor: James R. Berenson, West Hollywood, CA (US)

(73) Assignee: OncoTracker, Inc., West Hollywood, CA (US)

( * ) Notice: Subject to any disclaimer, the term of this patent is extended or adjusted under 35 U.S.C. 154(b) by 0 days.

(21) Appl. No.: 15/314,434

(22) PCT Filed: May 28, 2015

(86) PCT No.: PCT/US2015/032869
§ 371 (c)(1),
(2) Date: Nov. 28, 2016

(87) PCT Pub. No.: WO2015/184087
PCT Pub. Date: Dec. 3, 2015

(65) Prior Publication Data
US 2017/0106003 A1 Apr. 20, 2017

Related U.S. Application Data

(60) Provisional application No. 62/004,061, filed on May 28, 2014.

(51) Int. Cl.
*A61K 31/519* (2006.01)
*A61K 31/4523* (2006.01)
(Continued)

(52) U.S. Cl.
CPC .......... *A61K 31/573* (2013.01); *A61K 9/0053* (2013.01); *A61K 31/454* (2013.01); *A61K 31/519* (2013.01); *A61K 45/06* (2013.01)

(58) Field of Classification Search
CPC . A61K 31/519; A61K 31/4523; A61K 31/573
See application file for complete search history.

(56) References Cited

U.S. PATENT DOCUMENTS

| 5,712,291 A | 1/1998 | D'amato | |
| 2014/0135350 A1* | 5/2014 | Ni et al. | A61K 9/2054 |

FOREIGN PATENT DOCUMENTS

| WO | WO 2002/068414 A2 | 9/2002 |
| WO | WO 2008/154252 A1 | 12/2008 |

(Continued)

OTHER PUBLICATIONS

Rajkumar et al.; "Lenalidomide plus high-dose dexamethasone versus lenalidomide plus low-dose dexamethasone as initial therapy for newly diagnosed multiple myeloma: an open-label randomized controlled trial"; 2010; Lancet Oncol.; 11(1): 29-37.*

(Continued)

Primary Examiner — Timothy P Thomas
(74) Attorney, Agent, or Firm — Cooley LLP

(57) ABSTRACT

The present invention provides methods of treatment for hematological malignancies involving synergistic combination of a JAK2 inhibitor and a glucocorticoid or a JAK2 inhibitor, thalidomide or thalidomide derivative, and a glucocorticoid. The compositions and methods provide an unexpected efficacy in the treatment for hematological disorders. The hematological disorders treated by the current invention include multiple myeloma, and may also include hematological disorders that are refractory to prior cancer treatments, or a relapsed hematologic disorder.

24 Claims, 27 Drawing Sheets

(51) Int. Cl.
*A61K 31/473* (2006.01)
*A61K 31/573* (2006.01)
*A61K 31/454* (2006.01)
*A61K 45/06* (2006.01)
*A61K 9/00* (2006.01)

(56) References Cited

FOREIGN PATENT DOCUMENTS

| WO | WO-2012149602 A1 * | 11/2012 | ........... A61K 31/198 |
|---|---|---|---|
| WO | WO 2013/188783 A1 | 12/2013 | |

OTHER PUBLICATIONS

Chemocare; "Dexamethasone"; http://chemocare.com/chemotherapy/druginfo/dexamethasone.aspx; as evidenced by Wayback Machine capture on Mar. 8, 2013; https://web.archive.org/web/20130308085509/http://chemocare.com/chemotherapy/drug-info/dexamethasone.aspx; accessed Oct. 18, 2017.*

PCT/US2015/032869, International Search Report and Written Opinion dated Aug. 7, 2015, 10 pages.

PCT/US2015/032869, International Preliminary Report on Patentability dated Nov. 29, 2016, 8 pages.

Chou and Talalay, "Quantitative analysis of dose-effect relationships: the combined effects of multiple drugs or enzyme inhibitors." Adv Enzyme Regul. (1984); 22: 27-55.

Chen, Haiming, et al., "Anti-Myeloma Activity by the Combination of the JAK2 Inhibitor Ruxolitinib with Lenalidomide and Corticosteroids." Database accession No. PREV201500279383, Database Biosis [Online], Biosciences Information Service, Philadelphia, PA, US, Dec. 2014; & Blood, vol. 124, No. 21, Dec. 2014 (Dec. 2014), 56th Annual Meeting of the American Society of Hematology; San Francisco, CA, USA, Dec. 6-9, 2014, ISSN: 0006-4971 (print).

EP Application No. 15800211.3, Supplementary European Search Report dated Dec. 12, 2017, 21 pages.

Iris, Appleman, et al., "Prevention of Minimal Residual Disease in Ph plus AL", Database accession No. PREV201400360357, Database Biosis [Online], Biosciences Information Service, Philadelphia, PA, US, Nov. 2013; & Blood, vol. 122, No. 21, Nov. 2013 (Nov. 2013), p. 1265, 55th Annual Meeting of the American Society of Hematology; New Orleans, LA, USA, Dec. 7-10, 2013, ISSN: 0006-4971 (print).

Liu, T., et al., "Interleukin-6 and JAK2/STAT3 signaling mediate the reversion of dexamethasone resistance after dexamethasone withdrawal in 7TD1 multiple myeloma cells." Leukemia Research (2013); 37(10): 1322-1328.

Palumbo, A., et al., "Lenalidomide in combination with dexamethasone for the treatment of relapsed or refractory multiple myeloma." Blood Reviews (2009); 23(2): 87-93.

Pemovska, T., et al., "Individualized Systems Medicine Strategy to Tailor Treatments for Patients with Chemorefractory Acute Myeloid Leukemia." Cancer Discovery (2013); 13(12): 1416-1429.

Pemovska, T., et al., "Individualized Systems Medicine Strategy to Tailor Treatments for Patients with Chemorefractory Acute Myeloid Leukemia." Cancer Discovery (2013); 13(12): 1416-1429; Supplementary Materials. DOI: 10.1158/2159-8290.CD-13/0350 URL:http://cancerdiscovery.aacrjournals.org/content/candisc/suppl/2013/09/18/2159-8290.CD-1-0350.DC1/supp_figs_tables_and_methods.pdf.

Abou-Jawde, et al., "Efficacy and safety results with the combination therapy of arsenic trioxide, dexamethasone, and ascorbic acid in multiple myeloma patients: a phase 2 trial." Med Oncol. (2006); 23(2): 263-272.

Anonymous: ClinicalTrial.gov Identifier: NCT00258245, "Arsenic Trioxide and Ascorbic Acid Combined With Bortezomib, Thalidomide, and Dexamethasone in Treating Patients With Relapsed or Refractory Multiple Myeloma or Plasma Cell Leukemia—Tabular View—ClinicalTrials.gov", Apr. 29, 2013, pp. 1-13, XP055436992, Retrieved from the Internet: URL:https://clinicaltrials.gov/ct2/show/record/NCT00258245, [retrieved on Dec. 20, 2017], 13 pages.

Berenson, et al., "A phase I/II study of arsenic trioxide/bortezomib/ascorbic acid combination therapy for the treatment of relapsed or refractory multiple myeloma." Clin Cancer Res. (2007); 13(6): 1762-1768.

Crawford and Irvine, "Proteasome Inhibitors in the Treatment of Multiple Myeloma." In: "Multiple Myeloma—An Overview", (2012), InTech, XP055402864, 32 pages.

Rajkumar, et al., "Consensus recommendations for the uniform reporting of clinical trials: report of the International Myeloma Workshop Consensus Panel 1." Blood (2011); 117 (18):4691-4695.

Sharada, et al., "Intravenous dexamethasone pulse therapy in diffuse systemic sclerosis. A randomized placebo-controlled study." Rheumatology International (1994); 14 (3): 91-94.

* cited by examiner

A.

ANTI-CANCER EFFECTS OF JAK2 INHIBITORS IN COMBINATION WITH THALIDOMIDE DERIVATIVES AND GLUCOCORTICOIDS

CROSS REFERENCE TO RELATED APPLICATIONS

This application is a National Stage application, filed pursuant to 35 U.S.C. § 371, of International Application No. PCT/US2015/032869, filed on May 28, 2015, which claims the benefit under 35 U.S.C. § 119(e) of U.S. Provisional Application No. 62/004,061, filed May 28, 2014, which is incorporated by reference herein in its entirety.

BACKGROUND

Technical Field

The invention generally relates to novel methods of treating hematological malignancies, including multiple myeloma. More particularly the invention relates to methods of treating multiple myeloma with a JAK2 inhibitor, thalidomide or a derivative thereof, and/or a glucocorticoid.

Description of the Related Art

Multiple myeloma is a malignancy characterized by the expansion of plasma cells that produce monoclonal immunoglobulin (IgG, IgA, IgD, IgE, or free λ or κ light chains). The overall survival of patients with multiple myeloma varies greatly from a few months to many years; the mean is approximately five years. Anemia, hypercalcemia and bone lesions correlate directly with total mass of myeloma cells and have important prognostic significance. Other prognostic factors include age, the plasma cell labeling index, serum albumin, β2-microglobulin, C-reactive protein, thymidine kinase, and soluble interleukin 6 receptor. Major complications, such as infection and renal insufficiency, are the main causes of death for myeloma patients.

Current therapies for multiple myeloma fail to cure the disease and nearly all patients eventually develop resistance to these therapies. Moreover, there are a paucity of multiple myeloma targets and a lack of therapeutic options that are effective in overcoming drug resistance.

BRIEF SUMMARY

Figure 1:
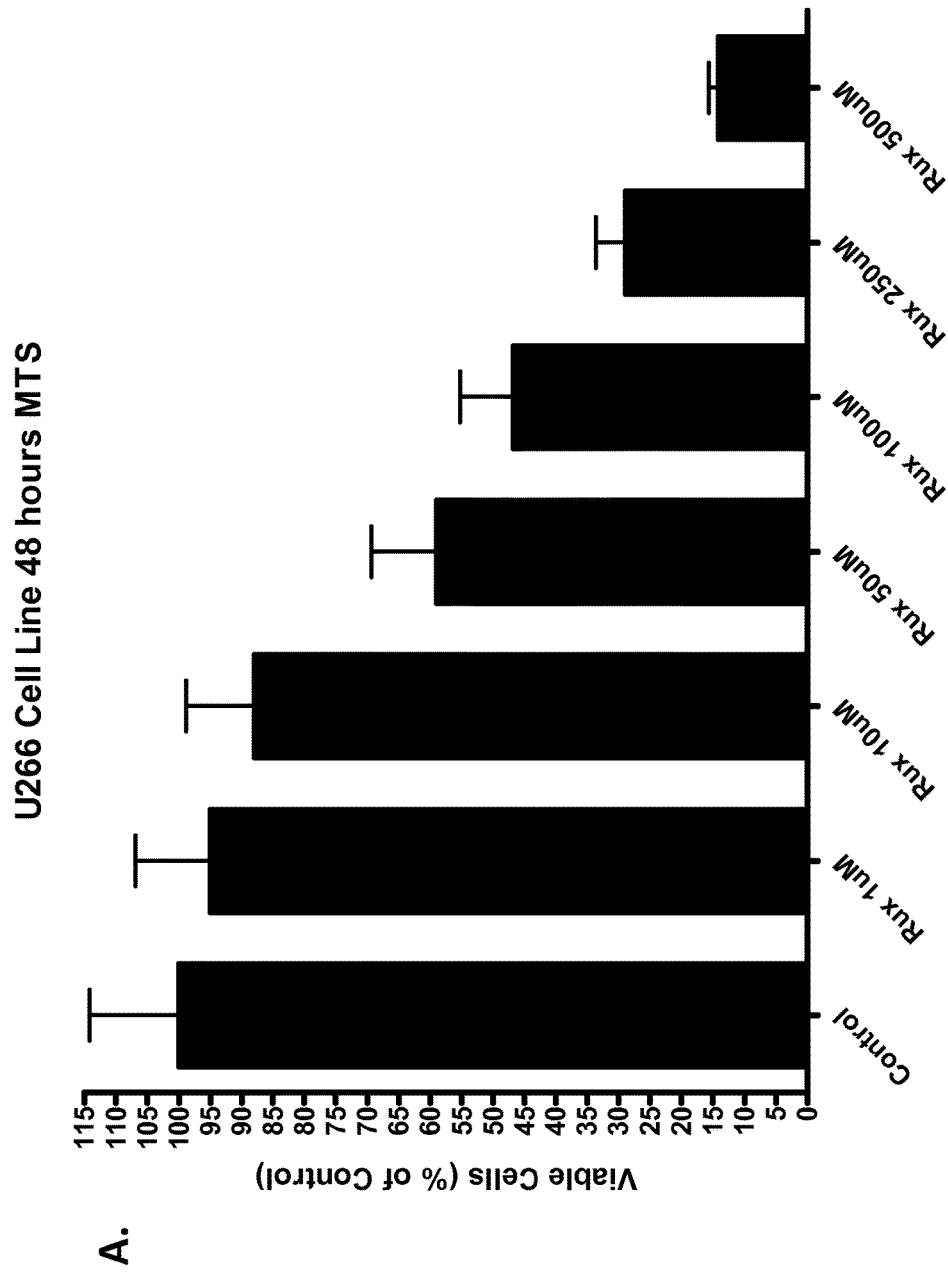
FIG. 1 shows a representative example of a multiple myeloma tumor cell viability assay of cells treated with a JAK2 inhibitor. The viability of A) U266 multiple myeloma tumor cells, B) RPMI8226 cells, and C) MM1 s cells was assessed by cell proliferation MTS assay following 48 hours of incubation with the indicated concentrations of the ruxolitinib.
Figure 1:
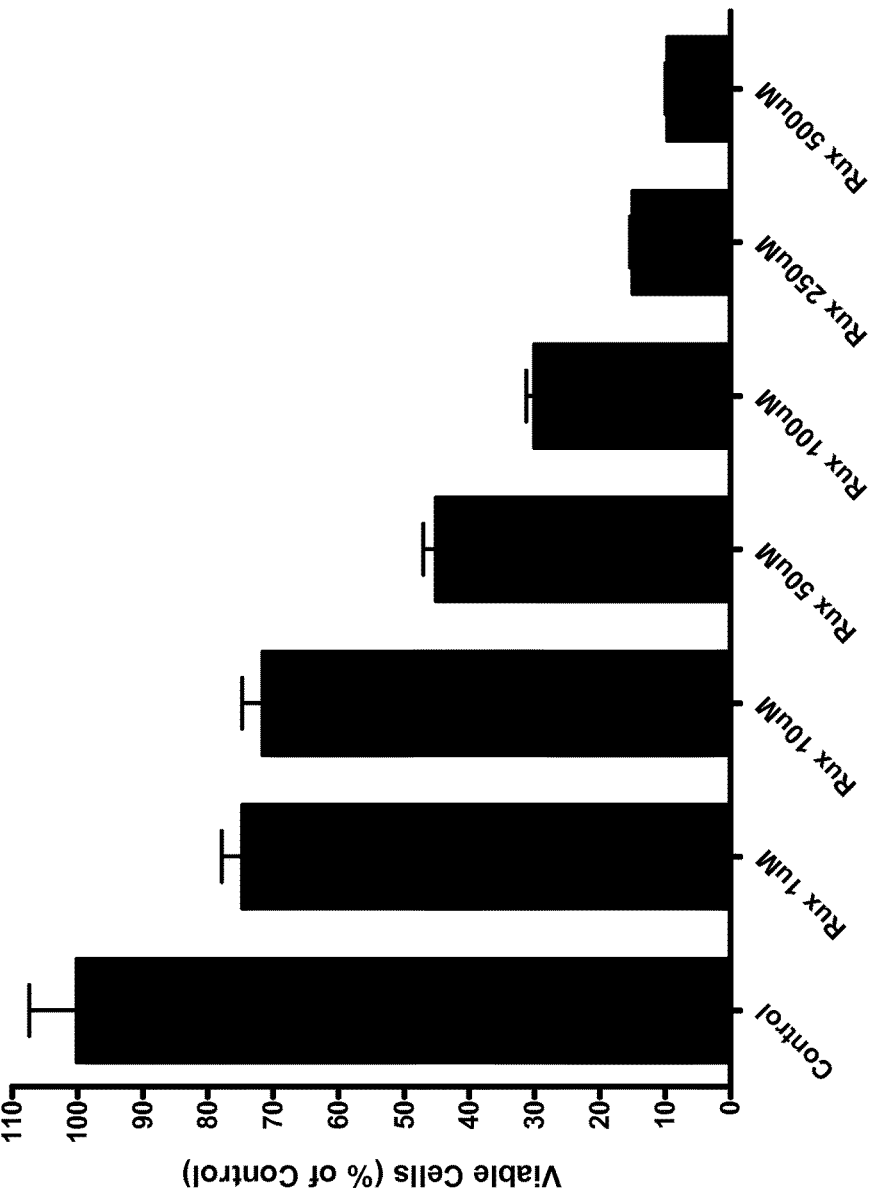
Figure 1:
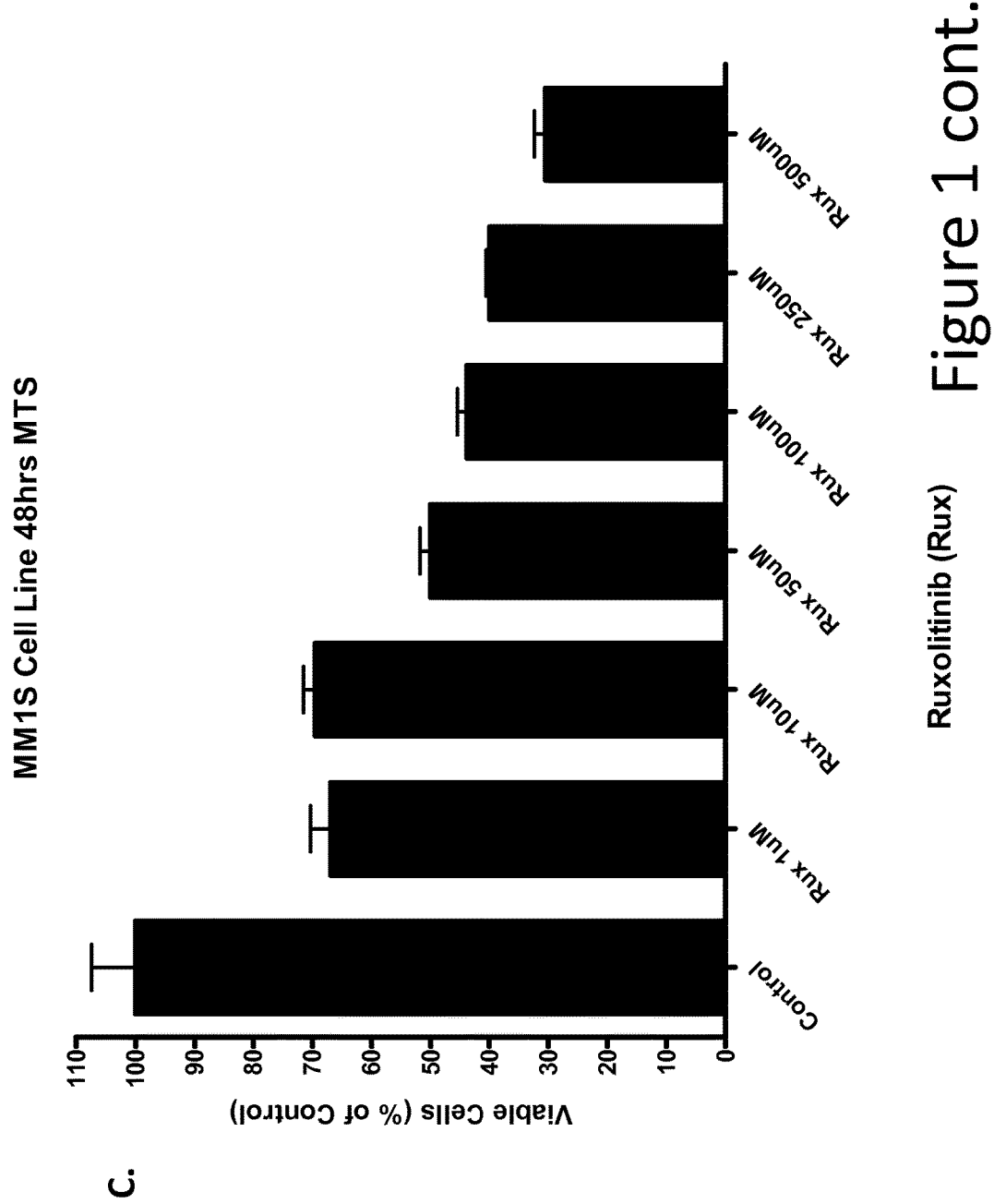

The present invention generally provides novel and synergistic treatments for multiple myeloma and related B cell disorders.

In various embodiments, a method of treating or preventing a hematological malignancy in a subject comprising administering to the subject a JAK2 inhibitor, and a glucocorticoid is provided.

In various other embodiments, a method of treating or preventing a hematological malignancy in a subject comprising administering to the subject a JAK2 inhibitor, thalidomide or a derivative thereof, and a glucocorticoid is provided.

In particular embodiments, the hematological malignancy is selected from the group consisting of: multiple myeloma, chronic lymphocytic leukemia, or B-cell non-Hodgkin lymphoma.

In certain embodiments, the JAK2 inhibitor is selected from the group consisting of: ruxolitinib, fedratinib, baricitinib, Pacritinib, AZD1480, XL019, LY2784544, BMS-911543, XL019, NS-018, CYT387, atiprimod dihydrochloride, CP 690550, Cucurbitacin I, 1,2,3,4,5,6-Hexabromocyclohexane, Lestaurtinib, NSC 33994, and SD 1008.

In particular embodiments, the JAK2 inhibitor comprises ruxolitinib.

In certain embodiments, thalidomide or the derivative thereof is selected from the group consisting of: thalidomide, lenalidomide, pomalidomide, linomide, CC-1088, CDC-501, and CDC-801.

In some embodiments, thalidomide derivative comprises lenalidomide.

In further embodiments, the glucocorticoid is selected from the group consisting of: hydroxycortisone, cortisone, desoxycorticosterone, fludrocortisone, betamethasone, dexamethasone, prednisolone, prednisone, methylprednisolone, methylprednisone, paramethasone, triamcinolone, flumethasone, fluocinolone, fluocinonide, fluprednisolone, halcinonide, flurandrenolide, meprednisone, and medrysone.

In particular embodiments, the glucocorticoid comprises dexamethasone.

In particular embodiments, the glucocorticoid comprises methylprednisolone.

In certain embodiments, the methods comprise administering: a) ruxolitinib and dexamethasone; or b) ruxolitinib and methylprednisolone, methylprednisone or prednisone; to the subject.

In additional embodiments, the methods comprise administering: a) ruxolitinib, lenalidomide, and dexamethasone; or b) ruxolitinib, lenalidomide, and methylprednisolone, methylprednisone or prednisone; to the subject.

In further embodiments, the methods comprise administering ruxolitinib orally.

In some embodiments, the methods comprise administering ruxolitinib at a dose of 1-50 mg.

In particular embodiments, the methods comprise administering lenalidomide orally.

In additional embodiments, the methods comprise administering lenalidomide at a dose of 1-50 mg.

In particular embodiments, the methods comprise administering dexamethasone intravenously.

In certain embodiments, the methods comprise administering dexamethasone orally.

In certain embodiments, the methods comprise administering dexamethasone at a dose of 1-100 mg.

In additional embodiments, the methods comprise administering methylprednisolone, methylprednisone or prednisone orally.

In particular embodiments, the methods comprise administering methylprednisolone, methylprednisone or prednisone at a dose of 1-100 mg.

In various embodiments, a method of treating or preventing multiple myeloma in a subject comprising administering to the subject a JAK2 inhibitor and a glucocorticoid is provided.

In various other embodiments, a method of treating or preventing multiple myeloma in a subject comprising administering to the subject a JAK2 inhibitor, thalidomide or a derivative thereof, and a glucocorticoid is provided.

In certain embodiments, the JAK2 inhibitor is selected from the group consisting of: ruxolitinib, fedratinib, baricitinib, Pacritinib, AZD1480, XL019, LY2784544, BMS-911543, XL019, NS-018, CYT387, atiprimod dihydrochloride, CP 690550, Cucurbitacin I, 1,2,3,4,5,6-Hexabromocyclohexane, Lestaurtinib, NSC 33994, and SD 1008.

In some embodiments, the JAK2 inhibitor comprises ruxolitinib.

In further embodiments, thalidomide or the derivative thereof is selected from the group consisting of: thalidomide, lenalidomide, pomalidomide, linomide, CC-1088, CDC-501, and CDC-801.

In certain embodiments, thalidomide or the derivative thereof comprises lenalidomide.

In certain embodiments, the glucocorticoid is selected from the group consisting of: hydroxycortisone, cortisone, desoxycorticosterone, fludrocortisone, betamethasone, dexamethasone, prednisolone, prednisone, methylprednisolone, methylprednisone, paramethasone, triamcinolone, flumethasone, fluocinolone, fluocinonide, fluprednisolone, halcinonide, flurandrenolide, meprednisone, medrysone, and esters and mixtures thereof.

In further embodiments, the glucocorticoid comprises dexamethasone.

In some embodiments, the glucocorticoid comprises methylprednisolone, methylprednisone, or prednisone.

In certain embodiments, a) ruxolitinib and dexamethasone; or b) ruxolitinib and methylprednisolone, methylprednisone or prednisone; are administered to the subject.

In further embodiments, a) ruxolitinib, lenalidomide, and dexamethasone; or b) ruxolitinib, lenalidomide, and methylprednisolone, methylprednisone or prednisone; are administered to the subject.

In particular embodiments, the methods comprise administering ruxolitinib orally.

In further embodiments, the methods comprise administering ruxolitinib at a dose of 1-50 mg.

In certain embodiments, the methods comprise administering lenalidomide orally.

In additional embodiments, the methods comprise administering lenalidomide at a dose of 1-50 mg.

In particular embodiments, the methods comprise administering dexamethasone intravenously.

In particular embodiments, the methods comprise administering dexamethasone orally.

In further embodiments, the methods comprise administering dexamethasone at a dose of 1-100 mg.

In certain embodiments, the methods comprise administering methylprednisolone, methylprednisone or prednisone orally.

In some embodiments, the methods comprise administering the methylprednisolone or methylprednisone at a dose of 1-100 mg.

In various embodiments, a method of treating or preventing a relapsed hematological malignancy in a subject comprising administering to the subject, a JAK2 inhibitor and a glucocorticoid is provided.

In other various embodiments, a method of treating or preventing a hematological malignancy that is refractory to prior treatment for cancer comprising administering to a subject, a JAK2 inhibitor and a glucocorticoid is provided.

In yet other various embodiments, a method of treating or preventing a relapsed hematological malignancy in a subject comprising administering to the subject, a JAK2 inhibitor, thalidomide or a derivative thereof, and a glucocorticoid is provided.

In still yet other various embodiments, a method of treating or preventing a hematological malignancy that is refractory to prior treatment for cancer comprising administering to a subject, a JAK2 inhibitor, thalidomide or a derivative thereof, and a glucocorticoid is provided.

In some embodiments, the hematological malignancy is selected from the group consisting of: multiple myeloma, chronic lymphocytic leukemia, or B-cell non-Hodgkin lymphoma.

In certain embodiments, the subject was previously treated with a chemotherapeutic agent.

In further embodiments, the subject was previously treated with doxorubicin or a derivative thereof, melphalan, etoposide, cytarabine, and bendamustine.

In further embodiments, the subject was previously treated with a proteasome inhibitor.

In certain embodiments, the subject was previously treated with bortezomib.

In some embodiments, the subject was previously treated with thalidomide or a derivative thereof.

In some embodiments, the subject was previously treated with a glucocorticoid.

In further embodiments, the subject was previously treated with thalidomide or a derivative thereof, and a glucocorticoid.

In certain embodiments, the subject was not previously treated with a JAK2 inhibitor, thalidomide or a derivative thereof, and a glucocorticoid.

In certain embodiments, the JAK2 inhibitor is selected from the group consisting of: ruxolitinib, fedratinib, baricitinib, Pacritinib, AZD1480, XL019, LY2784544, BMS-911543, XL019, NS-018, CYT387, atiprimod dihydrochloride, CP 690550, Cucurbitacin I, 1,2,3,4,5,6-Hexabromocyclohexane, Lestaurtinib, NSC 33994, and SD 1008.

In further embodiments, the JAK2 inhibitor comprises ruxolitinib.

In some embodiments, thalidomide or the derivative thereof is selected from the group consisting of: thalidomide, lenalidomide, pomalidomide, linomide, CC-1088, CDC-501, and CDC-801.

In certain embodiments, thalidomide or the derivative thereof comprises lenalidomide.

In further embodiments, the glucocorticoid is selected from the group consisting of: hydroxycortisone, cortisone, desoxycorticosterone, fludrocortisone, betamethasone, dexamethasone, prednisolone, prednisone, methylprednisolone, methylprednisone, paramethasone, triamcinolone, flumethasone, fluocinolone, fluocinonide, fluprednisolone, halcinonide, flurandrenolide, meprednisone, medrysone, and esters and mixtures thereof.

In some embodiments, the glucocorticoid comprises dexamethasone.

In further embodiments, the glucocorticoid comprises methylprednisolone, methylprednisone or prednisone.

In certain embodiments, ruxolitinib and dexamethasone; or ruxolitinib and methylprednisolone, methylprednisone, or prednisone; are administered to the subject.

In certain embodiment ruxolitinib, lenalidomide, and dexamethasone; or ruxolitinib, lenalidomide, and methylprednisolone, methylprednisone, or prednisone; are administered to the subject.

In particular embodiments, the methods comprise administering ruxolitinib orally.

In particular embodiments, the methods comprise administering ruxolitinib at a dose of 1-50 mg twice daily.

In some embodiments, the methods comprise administering lenalidomide orally.

In certain embodiments, the methods comprise administering lenalidomide at 1-50 mg.

In additional embodiments, the methods comprise administering dexamethasone intravenously.

In further embodiments, the methods comprise administering dexamethasone orally.

In additional embodiments, the methods comprise administering dexamethasone at 1-100 mg.

In particular embodiments, the methods comprise administering methylprednisolone, methylprednisone or prednisone orally.

In certain embodiments, the methods comprise administering methylprednisolone, methylprednisone or prednisone at a dose of 1-100 mg.

DETAILED DESCRIPTION

A. Introduction

Multiple myeloma is an incurable disease. Alkylating agents such as melphalan and cyclophosphamide and other drugs, including vinca alkaloids, nitrosoureas and anthracyclines, are only marginally effective in treating multiple myeloma when combined with steroids and do not improve survival compared to the combination of oral melphalan and prednisone. Nor has the commonly used combination of vincristine, doxorubicin and dexamethasone improved median survival compared to other treatment regimens in randomized clinical trials.

Proteasome inhibitors (PIs) such as bortezomib or carfilzomib, the immunomodulatory agents thalidomide, pomalidomide or lenalidomide, pegylated liposomal doxorubicin, and arsenic trioxide reduce myeloma cell growth in laboratory studies and have been used clinically to treat multiple myeloma patients. Initially, PIs were used alone, but recently these drugs have been combined with each other or with chemotherapy or glucocorticosteroids. High-dose chemotherapy followed by autologous hematopoietic support also represents another treatment option for multiple myeloma patients. Despite these recent improvements in multiple myeloma therapies, nearly all patients develop resistance to these therapies and eventually succumb to the disease.

In various embodiments, the present invention contemplates, in part, additional tumor targets and therapeutic options that are capable of overcoming drug resistance to hematological malignancies and improving the outcome for these patients. Surprisingly, the present inventors have discovered that using JAK2 inhibitors in combination with other drugs such as thalidomide or derivatives thereof, e.g. lenalidomide and/or glucocorticoids, provides a synergistic anti-cancer effect and may be used to treat patients with hematological malignancies and improve the clinical outcome. In particular embodiments, methods to prevent, ameliorate at least one symptom of, or treat hematological malignancies in a subject are provided.

In certain embodiments, subjects in need of treatment for a hematological malignancy including, but not limited to, chronic lymphocytic leukemias, B-cell non-Hodgkin lymphomas, and multiple myeloma are provided.

In various embodiments, a subject is administered a JAK2 inhibitor and a glucocorticoid to prevent, ameliorate at least one symptom of, or treat a hematological malignancy.

In various other embodiments, a subject is administered a JAK2 inhibitor, thalidomide or a derivative thereof, and a glucocorticoid to prevent, ameliorate at least one symptom of, or treat a hematological malignancy.

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2, or 1% to a reference quantity, level, value, number, frequency, percentage, dimension, size, amount, weight or length. In particular embodiments, the terms "about" or "approximately" when preceding a numerical value indicate the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "another embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The terms "treating," "treatment", and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest.

As used herein, the phrase "ameliorating at least one symptom of" refers to decreasing one or more symptoms of the disease or condition for which the subject is being treated. In particular embodiments, the disease or condition being treated is a hematological malignancy, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function). In particular embodiments, the disease or condition being treated is a multiple myeloma, wherein the one or more symptoms ameliorated include bone pain.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also include reducing the intensity, effect, symptoms and/or burden of a disease or condition prior to onset or recurrence of the disease or condition.

As used herein, the term "amount" refers to "an amount effective" or "an effective amount" of cells sufficient to achieve a beneficial or desired prophylactic or therapeutic result, including clinical results. In one embodiment an effect amount refers to the amount of a JAK2 inhibitor, thalidomide or a derivative thereof, and/or glucocorticoid sufficient to prevent, ameliorate one symptom of, or treat a disease, e.g., hematological malignancy contemplated herein.

A "prophylactically effective amount" refers to an amount of a JAK2 inhibitor, thalidomide or a derivative thereof, and/or glucocorticoid effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a JAK2 inhibitor, thalidomide or a derivative thereof, and/or glucocorticoid may vary according to factors such as the disease state, age, sex, and weight of the individual, and the agent to elicit a desired response in the individual. A therapeutically effective amount is also one in which any toxic or detrimental effects of the agent are outweighed by the therapeutically beneficial effects. The term "therapeutically effective amount" includes an amount that is effective to "treat" a subject (e.g., a patient).

As used herein, the terms "conditions sufficient," or "under conditions sufficient," refer to the conditions for treating the subject, with one or more agents or compositions contemplated herein. In one embodiment, "conditions sufficient" include administering a sufficient amount, e.g., an effective amount, of a JAK2 inhibitor, a glucocorticoid, and optionally thalidomide or a derivative thereof to a subject in need thereof.

As used herein, the terms "promoting," "enhancing," "stimulating," or "increasing" generally refer to the ability of compositions contemplated herein to produce or cause a greater physiological response (i.e., measurable downstream effect), as compared to the response caused by either vehicle or a control molecule/composition. One such measurable physiological response includes, without limitation, increased cell killing and/or tumor reduction, increased survival, increased treatment efficacy compared to normal, untreated, or control-treated subjects. The physiological response may be increased by at least 5%, 10%, 20%, 30%, 40%, 50%, 60%, 70%, 80%, 90%, 100%, 125%, 150%, 175%, 200%, or greater compared to the response measured in normal, untreated, or control-treated subjects. An "increased" or "enhanced" response or property is typically "statistically significant", and may include an increase that is 1.1, 1.2, 1.5, 2, 3, 4, 5, 6, 7, 8, 9, 10, 15, 20, 30, or more times (e.g., 500, 1000 times) (including all integers and decimal points in between and above 1, e.g., 1.5, 1.6, 1.7. 1.8, etc.) that produced by normal, untreated, or control-treated subjects.

As used herein, the terms "decrease" or "lower," or "lessen," or "reduce," or "abate" refers generally to the ability of compositions contemplated to produce or cause a lesser physiological response (i.e., downstream effects), as compared to the response caused by either vehicle or a control molecule/composition, e.g., decreased tumor volume. A "decrease" or "reduced" response is typically a "statistically significant" response, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by normal, untreated, or control-treated subject.

"Hematological malignancy" is a type of cancer that affects blood, bone marrow, or lymph nodes. Hematological malignancies may derive from either of the two major blood cell lineages: myeloid and lymphoid cell lines. The myeloid cell line normally produces granulocytes, erythrocytes, thrombocytes, macrophages, and mast cells, whereas the lymphoid cell lines produce B-cells, T-cells, natural killer cells, and plasma cells. Lymphomas, lymphocytic leukemias and myeloma are from the lymphoid cell lineage. Illustrative examples of hematological malignancies that can be treated with compositions contemplated herein include myelomas, leukemias and lymphomas. Other illustrative examples of hematological malignancies that are suitable for treatment in particular embodiments of the methods contemplated herein include, but are not limited to, multiple myeloma, acute myeloid leukemia (AML), chronic myeloid leukemia (CML), acute lymphatic leukemia (ALL), chronic lymphatic leukemia (CLL), Hodgkin's disease, non-Hodgkin lymphoma, myelodysplastic syndrome (MDS) or myeloproliferative diseases. Usually, hematological malignancies do not form solid tumors.

A "subject," "subject in need of treatment," "subject in need thereof," "individual," or "patient" as used herein, includes any animal that exhibits a symptom of a disease, disorder, or condition that can be treated with compositions contemplated herein. In particular embodiments, the disease, disorder, or condition relates to a hematological malignancy, e.g., multiple myeloma. Suitable subjects include laboratory animals (such as mouse, rat, rabbit, or guinea pig), farm animals (such as horses, cows, sheep, pigs), and domestic animals or pets (such as a cat or dog). In particular embodiments, the subject is a mammal. In certain embodiments, the subject is a non-human primate and, in preferred embodiments, the subject is a human.

The term "relapse" refers to the diagnosis of return, or signs and symptoms of return, of a cancer after a period of improvement or remission.

"Remission," also known as "clinical remission," includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

The term "agent" refers to a natural or synthetic polypeptide, polynucleotide, carbohydrate, fatty acid, chemical compound, or small organic molecule.

"Proteasome inhibitor" refers to any substance which directly or indirectly inhibits the 20S and/or 26S proteasome or an activity thereof. In particular embodiments, proteasome inhibition is specific, i.e., the proteasome inhibitor inhibits proteasome activity at a concentration that is lower than the concentration of the inhibitor required to produce another, unrelated biological effect. Illustrative examples of proteasome inhibitors that can be used in particular embodiments contemplated herein include, but are not limited to, bortezomib, carfilzomib, ONX 0912, CEP-18770, and MLN9708.

The term "small molecule" encompasses numerous biological and chemical classes, including synthetic, semi-synthetic, or naturally-occurring inorganic or organic molecules, including synthetic, recombinant or naturally-occurring compounds. A "small molecule" also refers to an agent that has a molecular weight of less than about 5 kD, less than about 4 kD, less than about 3 kD, less than about 2 kD, less than about 1 kD, or less than about 0.5kD. Small molecules include, but are not limited to: nucleic acids, peptidomimetics, peptoids, carbohydrates, lipids or other organic or inorganic molecules. In particular embodiments, small molecules are obtained from a combinatorial small organic molecule or peptide library containing a large number of potential therapeutic compounds. Such "combinatorial chemical libraries" or "ligand libraries" can be screened separately or screened in pools, to identify those library members of a particular chemical species or subclasses that display the desired characteristic activity of inhibiting JAK2 activity, possessing similar properties to thalidomide and its derivatives, or activating steroid receptors.

As used herein, the term "cell viability" refers to whether a cell is living or dead. Cell viability measurements may be used to evaluate the death or life of cells. Cell viability tests can be used to determine the effectiveness of agents to promote cell survival or induce cell death.

Cell proliferation MTS assay is an assay that depends on conversion of the MTS tetrazolium compound to a colored formazan product in metabolically active cells; it is therefore an assay of viable cell number. A decline in conversion of the tetrazolium compound relates to an increase in cell killing as long as cell disappearance by apoptosis in untreated cell populations is absent or negligible (as with most healthy primary cell populations).

"M-protein", also known as paraprotein, is an immunoglobulin or immunoglobulin light-chain that is produced in excess by the clonal proliferation of monoclonal plasma cells. Detection of paraproteins in the urine or blood can be associated with multiple myeloma.

"Immunoglobulin isotypes" refer to genetic variations or differences in the constant regions of the heavy and light chains. In humans, there are five heavy chain isotypes; IgA, IgD, IgG, IgE, and IgM; and two light chains: or K light chains.

"Platelets" are small cells found in blood. Platelets are cytosolic fragments that do not contain nuclei that are generated from megakaryocytes of the bone marrow. Platelets function, along with coagulation factors, to stop or prevent bleeding. In hematological malignancies, such as multiple myeloma, platelets levels are often reduced.

"Hematocrit", also known in the art as "packed cell volume" or "erythrocyte volume fraction" is the ratio of the total volume of the red cells (erythrocytes) of a given sample of whole blood to the total volume of that sample, normally expressed as a percentage. This index is useful in diagnostic studies and treatment of diseases whose symptoms and manifestations may include physical changes in the blood. The measurement depends on the number and size of the erythrocytes.

"Hemoglobin" is a protein that functions physiologically as the principal carrier of oxygen in whole blood from the lungs to other body tissues. It is also the protein found in highest concentration in whole blood (normally 12-18 percent). Lower than normal values are symptomatic of anemia, which is commonly associated with multiple myeloma. The determination of hemoglobin content of whole blood is done routinely and, thus, is one of the most frequently performed clinical laboratory tests.

A "treatment cycle" as used herein refers to a course of treatment that is repeated on a regular schedule. A treatment cycle can comprise several days of treatment followed by several days of rest. For example, an agent may be administered daily for three weeks, followed by a week of no treatment, in a 28-day treatment cycle.

C. Compositions

In various embodiments, a subject is administered one or more of the compositions contemplated herein to prevent, ameliorate at least one symptom of, or treat a hematological malignancy. In particular embodiments, a subject is administered one or more compositions comprising a JAK2 inhibitor and a glucocorticoid. In certain embodiments, a subject is administered one or more compositions comprising a JAK2 inhibitor, a glucocorticoid, and thalidomide or a derivative thereof. In various embodiments, the compositions contemplated herein comprise one or more JAK2 inhibitors, thalidomide or derivatives thereof, and/or glucocorticoids that can be administered separately or in any suitable combination are administered to prevent, ameliorate at least one symptom of, or treat a hematological malignancy.

In one embodiment, a composition contemplated herein comprises a JAK2 inhibitor, thalidomide or a derivative thereof, or a glucocorticoid. In another embodiment, a composition contemplated herein comprises a JAK2 inhibitor and thalidomide or derivative thereof; a JAK2 inhibitor and a glucocorticoid; or thalidomide or a derivative thereof and a glucocorticoid. In yet another embodiment, a composition contemplated herein preferably comprises a JAK2 inhibitor, thalidomide or a derivative thereof, and a glucocorticoid. The compositions may be administered separately or together at the same time or at different times in any suitable combination.

The present inventors have discovered that JAK2 inhibitors, when combined with glucocorticoids, or when combined with glucocorticoids and thalidomide derivatives, are unexpectedly and synergistically effective at treating hematological malignancies. Without being bound to any particular theory, the present invention contemplates, in part, that the JAK2 inhibitors when combined glucocorticoids, or when combined with glucocorticoids and thalidomide derivatives thereof, are more effective for treating a hematological malignancy in a subject than either of JAK2 inhibitors, glucocorticoids, or thalidomide or derivatives thereof alone.

According to some embodiments, JAK2 inhibitors of the invention are useful for treating cancer when combined with a glucocorticoid or in combination with a glucocorticoid and a thalidomide or derivative thereof, and administered to a subject diagnosed with hematological malignancies. In some embodiments, the hematological malignancies can include, but are not limited to multiple myeloma, chronic lymphocytic leukemia, or B-call non-Hodgkin lymphoma. In some embodiments, the hematological malignancy is refractory to previous treatments for cancer. These previous treatments may include, but are not limited to, chemotherapeutic agents or proteasome inhibitors. In some embodiments, the hematological malignancy is relapsed.

In particular embodiments, compositions (i.e., medicaments) contemplated herein comprise one or more of JAK2 inhibitors, thalidomide or derivatives thereof, and glucocorticoids. In certain embodiments, the one or more of JAK2 inhibitors, thalidomide or derivatives thereof, and glucocorticoids may be delivered in the form of a prodrug, solvate, stereoisomer, racemate, tautomer or pharmaceutically-acceptable salt thereof.

As used herein, the term "prodrug" refers to a compound that may be converted under physiological conditions or by solvolysis to a biologically active compound contemplated herein. In one embodiment, the term "prodrug" refers to a pharmaceutically acceptable metabolic precursor of a compound contemplated herein. A prodrug may be inactive when administered, but converted in vivo to an active compound o. Prodrugs are typically rapidly transformed in vivo to yield a JAK2 inhibitor, thalidomide or derivative thereof, or a corticoid steroid, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., A.C.S. Symposium Series, Vol. 14, and in *Bioreversible Carriers in Drug Design*, Ed. Edward B. Roche, American Pharmaceutical Association and Pergamon Press, 1987. In certain embodiments, the term "prodrug" also refers to any covalently bonded carriers, which release the active compound of the invention in vivo when such prodrug is administered to a mammalian subject. Prodrugs contemplated herein may be prepared by modifying functional groups present in the compound in such a way that the modifications are cleaved, either in routine manipulation or in vivo, to the parent compound. Prodrugs may comprise compounds wherein a hydroxy, amino or mercapto group is bonded to any group that, when the prodrug is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds and the like.

In particular embodiments, the compounds contemplated herein may be isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively.

D. Janus Kinase 2 Inhibitors

The Janus family of kinases is among the JAK1, JAK2, JAK3, and Tyk2cytoplasmic protein tyrosine kinases. JAK kinases play a major role in the transmission of signals from cytokine and growth factor receptors into the nucleus. JAK kinases activate several intracellular signaling proteins, among which the STAT transcription factors are well defined. The JAK/STAT pathway mediates diverse cellular events that affect cell growth, differentiation and cell survival.

Abnormal activation of JAK2 has been implicated in several hematological disorders and malignancies. JAK2 can be aberrantly activated by cytokines released through bone marrow stromal cells, or by mutation or translocation that directly affect the JAK2 gene. The JAK2 V617F mutation results in unchecked JAK2 activation causing uncontrolled cytokine and growth factor signaling and is believed to play a role in the pathophysiology of myeloproliferative neoplasms. JAK2 can also become constitutively active through specific chromosomal translocations, which contribute to the development of leukemias, lymphomas and myelomas.

Another cause of increased JAK2 activity in multiple myeloma can be the elevated levels of cytokines and growth factors such as interleukin-6 (IL-6), vascular endothelial growth factor (VEGF), insulin-like growth factor-1, basic fibroblast growth factor, IL-1, IL-10, IL-11, IL-15, IL-21, granulocyte macrophage colony-stimulation factor (GM-CSF), interferon-α, and leukemia inhibitory factor. Among these cytokines, IL-6 has been most widely studied and is considered to play a role as a growth and survival factor for myeloma cells. Binding of IL-6 to the IL-6 receptor activates JAK2, which in turn can phosphorylate the IL-6 receptor and augment its downstream signaling effects.

In various embodiments, a subject is administered a JAK2 inhibitor, optionally in combination with thalidomide or a derivative thereof, and/or a glucocorticoid. Without being bound to any particular theory, the present invention contemplates, in part, that JAK2 inhibitors combined glucocorticoids, or combined with glucocorticoids and thalidomide or derivatives thereof, synergistically treat a hematological malignancy compared to JAK2 inhibitors, glucocorticoids, or thalidomides or derivatives thereof alone.

In particular embodiments, a JAK2 inhibitor suitable for use in the compositions and methods contemplated herein includes any agent that inhibits JAK2 activity. In certain embodiments, a JAK2 inhibitor may decrease JAK2 activity about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, compared to JAK2 that has not been contacted by the JAK2 inhibitor.

In particular embodiments, a JAK2 inhibitor may decrease levels of JAK2 protein about 5%, about 10%, about 15%, about 20%, about 25%, about 30%, about 30%, about 35%, about 40%, about 45%, about 50%, about 55%, about 60%, about 65%, about 70%, about 75%, about 80%, about 85%, about 90%, about 95%, about 100%, compared to the level of JAK2 in a cell or cells that have not been contacted by the JAK2 inhibitor.

JAK2 activity can be determined by determining levels of JAK2 in known active or inactive conformations, comparing phosphorylation of known targets of JAK2 phosphorylation, and/or determining levels of JAK2 protein or the like.

Illustrative examples of JAK2 inhibitors suitable for use in particular embodiments contemplated herein, include, but are not limited to ruxolitinib, fedratinib, baricitinib, pacritinib, AZD1480, XL019, LY2784544, BMS-911543, XL019, NS-018, CYT387, atiprimod dihydrochloride, CP-690550, cucurbitacin I, 1,2,3,4,5,6-hexabromocyclohexane, lestaurtinib, NSC 33994, and SD 1008.

In one embodiment, the JAK2 inhibitor administered to a subject is ruxolitinib or CP-690550.

E. Glucocorticoids

Glucocorticoids contemplated herein are useful for treating cancer in a subject diagnosed with hematological malignancies. In particular embodiments, glucocorticoid treatment of hematological malignancies is combined with treatment with thalidomide or a derivative thereof, and/or a JAK2 inhibitor. Without wishing to be bound to any particular theory, glucocorticoids may exert anticancer effects, in part, through activation of endogenous steroid receptors, including but not limited to glucocorticoid receptors.

In particular embodiments, a glucocorticoid activates a steroid receptor, e.g., glucocorticoid receptor to increase steroid receptor activity about 5%, about 10%, about 15%, about 20%, about 25%, about 30%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, or about two-fold, about three-fold, four-fold, about five-fold, about ten-fold, about twenty-fold, about thirty-fold, about forty-fold, about fifty-fold, about sixty-fold, about seventy-fold, about eighty-fold, about ninety-fold, or about one hundred-fold or greater. Activity of the steroid receptor may be determined by one or more methods including, but not limited to, measuring translocation of the steroid receptor from one cellular compartment to another (e.g. translocation from cytosol to the nucleus), measuring the gene product of a gene that is transcribed as a result of steroid receptor activation, or measuring amount of steroid receptor in an active confirmation, as compared to steroid receptors that are not contacted by the agent.

Illustrative examples of glucocorticoids and glucocorticoid receptor agonists suitable for use in the compositions and methods contemplated herein include, but are not limited to, medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol, as well as combinations thereof.

In one embodiment, the glucocorticoid administered to a subject is dexamethasone, methylprednisolone, methylprednisone, or prednisone but not limited to these glucocorticoids.

F. Thalidomide and Derivatives Thereof

In the late 1950s and early 1960s, thalidomide was marketed as an over-the-counter sedative, tranquilizer, and treatment for morning sickness until it was discovered that thalidomide caused severe teratogenic birth defects. However, interest in the drug reemerged in the 1990s when studies demonstrated thalidomide had properties that could be effective in treatment for cancer.

Thalidomide and its derivatives have been shown to upregulate several cyclin dependent kinase inhibitors (CDKNs), including CDKN1A (p21$^{CIP1}$), CDKN1B (P27$^{KIP1}$), CDKN2A (p16$^{INK4A}$) and CDKN2B (p15$^{INK4B}$). Thalidomide derivatives have also been shown to alter the immunological profile of the tumor microenvironment by inhibiting release of TNFalpha, IL-1beta, and IL6, factors that have been implicated in stimulating growth and survival in cancer cells.

In particular embodiments, treatment of hematological malignancies with thalidomide or a derivative thereof is combined with glucocorticoid treatment or and/or a JAK2 inhibitor treatment.

The term "thalidomide" refers to drugs or pharmaceutical formulations comprising the active thalidomide compound 2-(2,6-dioxopiperidin-3-yl)-1H-isoindole-1,3(2H)-dione.

The term "thalidomide derivative" or thalidomide or "derivatives thereof" refers to structural variants of thalidomide that have a similar biological activity such as, for example, without limitation, lenalidomide (REVLIMID™) ACTIMID™ (Celgene Corporation), and POMALYST™ (Celgene Corporation), and the compounds disclosed in U.S.

Pat. No. 5,712,291, WO02068414, and WO2008154252, each of which is incorporated herein by reference in its entirety.

Illustrative examples of thalidomide or derivatives thereof suitable for use in particular embodiments contemplated herein include, but are not limited to, thalidomide, lenalidomide, pomalidomide, linomide, CC-1088, CDC-501, and CDC-801.

In one embodiment, the subject is administered the thalidomide derivative lenalidomide.

G. Pharmaceutical Compositions and Formulations

Compositions (i.e., medicaments) contemplated herein include, but are not limited to pharmaceutical compositions. A "pharmaceutical composition" refers to a formulation of a composition with one or more pharmaceutically acceptable carriers, diluents or excipients generally accepted in the art for the delivery of a compound or drug to a mammal, e.g., humans. In particular embodiments, pharmaceutical compositions comprise a JAK2 inhibitor and a glucocorticoid, or a JAK2 inhibitor, glucocorticoid, and thalidomide or a derivative thereof, formulated with one or more pharmaceutically-acceptable carriers, diluents, and/or excipients. It will also be understood that, if desired, the compositions of the invention may be administered in combination with other agents as well, such as, e.g., nucleic acids, proteins, small molecules, or pharmaceutically-active agents, adjunct therapies, etc. so long as the desired therapeutic effect is achieved. There is virtually no limit to other reagents that may also be included in the compositions, provided that the additional reagents do not adversely affect the desired cancer therapy.

In particular embodiments, compositions comprise pharmaceutically acceptable formulations with therapeutically effective amounts of JAK2 inhibitors, glucocorticoids, and/or thalidomide or derivatives thereof; or prodrugs, solvates, stereoisomers, racemates, or tautomers of JAK2 inhibitors, glucocorticoids, and/or thalidomide or derivative thereof, formulated with one or more pharmaceutically acceptable carriers (additives), other active agents, and/or diluents.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compounds contemplated herein exist in free base or acid form and can be converted to their pharmaceutically acceptable salts by treatment with the appropriate inorganic or organic base or acid by methods known to one skilled in the art. "Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Salts of the compounds of the invention can be converted to their free base or acid form by standard techniques.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In particular embodiments, a pharmaceutical composition contemplated herein is formulated so as to allow the active ingredients contained therein to be bioavailable upon administration of the composition to a subject. In one embodiment, pharmaceutical compositions can be prepared by combining JAK2 inhibitors, glucocorticoids, and/or thalidomide or derivatives thereof, with an appropriate pharmaceutically acceptable carrier, diluent or excipient, and may be formulated into preparations in solid, semisolid, liquid, gels, and microspheres. However, in certain embodiments the subject compounds may be simply dissolved or suspended in sterile water of physiological saline, Ringer's solution, or 0.9% NaCl.

Solid formulations of the compositions contemplated herein, include dragees, capsules, pills and granules, optionally scored or prepared with coatings and shells, such as enteric coatings and other coatings. Solid dosage forms may also be formulated so as to provide slow or controlled release of the compound. Thus, solid formulations could include any material that could provide a desired release profile of the compound, including but not limited to hydroxypropylmethyl cellulose in varying proportions, or other polymer matrices, liposomes and/or microspheres.

Coated, gel, or encapsulating formulations of JAK2 inhibitors, glucocorticoids, and/or thalidomide or derivatives thereof may also be formulated to deliver pulsatile, sustained, or extended release. For example, one method of pulsatile release could be achieved by layering multiple coatings of JAK2 inhibitors, glucocorticoids, and/or thalidomide or derivatives thereof, or by incorporating JAK2 inhibitors, glucocorticoids, and/or thalidomide or derivatives thereof within different regions of the formulation having different release times.

Liquid dosage formulations contemplated herein include pharmaceutically acceptable emulsions, microemulsions, solutions, suspensions, syrups and elixirs. In addition, the liquid dosage formulations may contain inert diluents commonly used in the art, including but not limited to water or other solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol; oils (in particular, cottonseed, groundnut, corn, germ, olive, castor and sesame oils); glycerol; tetrahydrofuryl alcohol; polyethylene glycols; and fatty acid esters of sorbitan, and mixtures thereof.

Suspensions formulations include, without limitation, ethoxylated isostearyl alcohols; polyoxyethylene sorbitol and sorbitan esters; microcrystalline cellulose; aluminum metahydroxide; bentonite; agar-agar; tragacanth; and mixtures thereof.

Injectable depot formulations can be made by forming microencapsulated matrices of the composition in biodegradable polymers. Examples of biodegradable polymers include, but are not limited to polylactide-polyglycolide, poly(orthoesters) and poly(anhydrides). The ratio of composition to polymer and the nature of the particular polymer employed can affect the rate of release of JAK2 inhibitors, glucocorticoids, and/or thalidomide or derivatives thereof from the composition. Depot injectable formulations can also be prepared by entrapping the drug in liposomes or microemulsions.

Proper fluidity of liquid, suspension and other formulations of the compounds can be maintained by the use of coating materials such as lecithin; by the maintenance of the required particle size in the case of dispersions; or by the use of surfactants.

Formulations may also include anti-contamination agents for the prevention of microorganism contamination. Anti-contamination agents may include but are not limited to antibacterial and antifungal agents, for example, paraben, chlorobutanol, phenol sorbic acid, antibiotics, and the like.

Formulations may also be sterilized by, for example, by filtration through a bacteria-retaining filter, or by incorporating sterilizing agents in the form of sterile solid formulations which can be dissolved in sterile water, or some other sterile medium immediately before use or formulation.

Formulations may also be endotoxin free. As used herein, the term "endotoxin free" refers to compositions or formulations that contain at most trace amounts (i.e., amounts having no adverse physiological effects to a subject) of endotoxin, and preferably undetectable amounts of endotoxin. By "substantially free of endotoxin" is meant that there is less endotoxin per dose of cells than is allowed by the FDA for a biologic, which is a total endotoxin of 5 EU/kg body weight per day, which for an average 70 kg person is 350 EU per total dose of cells. In one embodiment, the term "endotoxin free" refers to a composition or formulation that is at least 95%, at least 96%, at least 97%, at least 98%, at least 99%, or 100% endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts may cause adverse effects in humans.

Pharmaceutical compositions may further comprise one or more components that enhance the bioavailability of the active ingredients of the composition, e.g., penetration enhancers, stabilizing agents, and one or more components that provide slow or controlled release of the JAK2 inhibitors, glucocorticoids, and/or thalidomide or derivatives thereof in the composition, e.g., biocompatible polymers and/or gels.

In particular embodiments, compositions comprising penetration enhancers will facilitate the delivery of the composition across biological barriers. A "penetration enhancer" or "permeability enhancer" includes a polyol such as polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxysalicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauric acid, oleic acid, undecanoic acid and methyl oleate, fatty alcohols, such as octanol and nonanol, laurocapram, cyclodextrins, thymol, limonene, urea, chitosan and other natural and synthetic polymers.

Suitable polyols for inclusion in the solutions include glycerol and sugar alcohols such as sorbitol, mannitol or xylitol, polyethylene glycol and derivatives thereof. In some embodiments the composition further includes a preservative. Accepted preservatives such as benzalkonium chloride and disodium edetate (EDTA) are included in the compositions of the invention in concentrations sufficient for effective antimicrobial action, about 0.0001 to 0.1%, based on the weight of the composition.

In particular embodiments, compositions comprise stabilizers to increase the therapeutic lifetime of the compositions in vivo. Exemplary stabilizers include fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In further embodiments, the chosen stabilizer changes the hydrophobicity of the formulation (e.g., oleic acid, waxes), or improves the mixing of various components in the formulation (e.g., ethanol), affects the moisture level in the formula (e.g., PVP or polyvinyl pyrrolidone), affects the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In other embodiments, stabilizers are present in sufficient amounts to inhibit the degradation of the JAK2 inhibitors, glucocorticoids, and/or thalidomide or derivatives thereof in a composition. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In particular embodiments, compositions are formulated as controlled release formulations. In general, controlled release drug formulations impart control over the release of drug with respect to site of release and time of release in vivo. Controlled release includes immediate release, delayed release, sustained release, extended release, variable release, pulsatile release, and bi-modal release. Advantages offered by controlled release include: less frequent dosing; more efficient drug utilization; localized drug delivery by placement of a delivery device or formulation at a treatment site in vivo; and the opportunity to administer and release two or more different drugs, each having a unique release profile, or to release the same drug at different rates or for different durations, by means of a single dosage unit.

Controlled release formulations may be made by formulating the compositions with biocompatible polymers, viscosity agents, gels, paints, foams, xerogels, microparticles, hydrogels, nanocapsules, and thermoreversible gels, or combinations thereof. In particular embodiments, the polymer or gels are biodegradable. Release properties are often controlled by the particular combination of polymers or gels used to formulate the composition. These methods are well known in the art.

Exemplary polymers suitable for formulating the inventive compositions include, but are not limited to polyamides, polycarbonates, polyalkylenes (polyethylene glycol (PEG)), polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly (valeric acid), poly(lactide-co-caprolactone), polysaccharides, proteins, polyhyaluronic acids, polycyanoacrylates, and blends, mixtures, or copolymers thereof.

In particular embodiments, the polymer is a ABA-type or BAB-type triblock copolymers or mixtures thereof, wherein the A-blocks are relatively hydrophobic and comprise biodegradable polyesters or poly(orthoester), and the B-blocks are relatively hydrophilic and comprise polyethylene glycol (PEG). The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof.

Exemplary viscosity agents suitable for use in formulating compositions include, but are not limited to, hydroxypropyl methylcellulose, hydroxyethyl cellulose, polyvinylpyrrolidone, carboxymethyl cellulose, polyvinyl alcohol, sodium chondroitin sulfate, sodium hyaluronate, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, or polyvinylpyrrolidone (PVP: povidone).

Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, glycerin-based gels, glycerin-derived compounds, conjugated, or crosslinked gels, matrices, hydrogels, and polymers, as well as gelatins and their derivatives, and various native and synthetic hydrogel and hydrogel-derived compounds, and any combinations or mixtures thereof.

In a particular embodiment, compositions contemplated herein comprise an effective amount of a JAK2 inhibitor, thalidomide or a derivative thereof, and/or a glucocorticoid, alone or in combination with one or more other therapeutic agents or modalities. Thus, the compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, NSAIDs, DMARDs, anti-inflammatories, chemotherapeutics, radiotherapeutics, therapeutic antibodies, or other active and ancillary agents.

In certain embodiments, compositions contemplated herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin and its pegylated formulations, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions contemplated herein. In one embodiment, the compositions contemplated herein are administered with nonsteroidal anti-inflammatory drugs (NSAIDS) including aspirin, ibuprofen, naproxen, methotrexate, sulfasalazine, leflunomide, anti-TNF medications, cyclophosphamide, and mycophenolate.

Other exemplary NSAIDs are chosen from the group consisting of ibuprofen, naproxen, naproxen sodium, COX-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers, cytokine inhibitors, such as the TNF antagonists, adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline. Illustrative examples of therapeutic antibodies suitable for combination with compositions contemplated herein, include but are not limited to, bavituximab, bevacizumab (avastin), bivatuzumab, blinatumomab, conatumumab, daratumumab, duligotumab, dacetuzumab, dalotuzumab, elotuzumab (HuLuc63), gemtuzumab, ibritumomab, indatuximab, inotuzumab, lorvotuzumab, lucatumumab, milatuzumab, moxetumomab, ocaratuzumab, ofatumumab, rituximab, siltuximab, teprotumumab, and ublituximab.

In certain embodiments, the compositions described herein are administered in conjunction with one or more cytokines. A "cytokine" refers to proteins released by one cell population that act on another cell as intercellular mediators. Illustrative examples of such cytokines are lymphokines, monokines, and traditional polypeptide hormones. Included among the cytokines are growth hormones such as human growth hormone, hepatic growth factor; tumor necrosis factor-alpha and -beta; mullerian-inhibiting substance; inhibin; activin; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In particular embodiments, the compositions contemplated herein comprise a concentration of one or more pharmaceutically active ingredients (i.e., JAK2 inhibitors, glucocorticoids, and thalidomides or derivatives thereof; and optionally pharmaceutically acceptable salts, prodrugs, solvates, stereoisomers, racemates, or tautomers thereof) of between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of each active ingredient, by weight of the composition.

In certain embodiments, the compositions described herein have a concentration of each active pharmaceutical agent between about 1% to about 50%, between about 5% to about 50%, between about 10% to about 40%, or between about 10% to about 30%, of the active ingredient, or pharmaceutically acceptable salt, prodrug, solvate, stereoisomer, racemate, or tautomer thereof, by weight of the composition.

In some embodiments, the formulations have a concentration of active pharmaceutical ingredient of between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable salt, prodrug, solvate, stereoisomer, racemate, or tautomer thereof, by volume of the formulation.

In one embodiment, the formulations additionally provide an immediate release of one or more pharmaceutically active ingredients (i.e., JAK2 inhibitors, glucocorticoids, and/or thalidomide or derivatives thereof, or pharmaceutically acceptable salts, prodrugs, solvates, stereoisomers, racemates, or tautomers thereof) from the composition, or within 1 minute, or within 5 minutes, or within 10 minutes, or within 15 minutes, or within 30 minutes, or within 60 minutes or within 90 minutes.

In another embodiment, a therapeutically effective amount of at least one pharmaceutically active ingredient is released from the composition immediately, or within 1 minute, or within 5 minutes, or within 10 minutes, or within 15 minutes, or within 30 minutes, or within 60 minutes or within 90 minutes.

In yet another embodiment, a composition is formulated as an extended release formulation. In certain embodiments, diffusion of at least one pharmaceutically active ingredient from the formulation occurs for a time period exceeding 5 minutes, 15 minutes, 30 minutes, 1 hour, 4 hours, 6 hours, 12 hours, 18 hours, 1 day, 2 days, 3 days, 4 days, 5 days, 6 days, 7 days, 10 days, 12 days, 14 days, 18 days, 21 days, 25 days, 30 days, 45 days, 2 months 3 months 4 months 5 months 6 months 9 months or 1 year.

In particular embodiments, a therapeutically effective amount of at least one pharmaceutically active ingredient is released from the formulation for a time period exceeding 5 minutes, 15 minutes, 30 minutes, 1 hour, 4 hours, 6 hours, 12 hours, 18 hours, 1 day, 2 days, 3 days, 4 days, 5 days, 6 days, 7 days, 10 days, 12 days, 14 days, 18 days, 21 days, 25 days, 30 days, 45 days, 2 months 3 months 4 months 5 months 6 months 9 months or 1 year.

In further embodiments, the formulation provides both an immediate release and an extended release formulation. In particular embodiments, the formulation contains a 0.25:1 ratio, a 0.5:1 ratio, a 1:1 ratio, a 1:2 ratio, a 1:3, a 1:4 ratio, a 1:5 ratio, a 1:7 ratio, a 1:10 ratio, a 1:15 ratio, or a 1:20 ratio of immediate release and extended release formulations. In a further embodiment the formulation provides an immediate release of a first pharmaceutically active ingredient and an extended release of a second pharmaceutically active ingredient or other therapeutic agent.

In additional embodiments, the formulation provides a 0.25:1 ratio, a 0.5:1 ratio, a 1:1 ratio, a 1:2 ratio, a 1:3, a 1:4 ratio, a 1:5 ratio, a 1:7 ratio, a 1:10 ratio, a 1:15 ratio, or a 1:20 ratio of immediate release and extended release formulations of one or more pharmaceutically active ingredients.

The combination of immediate release, delayed release and/or extended release compositions or formulations may be combined with other pharmaceutical agents, as well as the excipients, diluents, stabilizers, carrier agents and other components disclosed elsewhere herein. As such, depending upon the components of a composition, the thickness or viscosity desired, or the mode of delivery chosen, alternative aspects of the embodiments disclosed herein are combined with the immediate release, delayed release and/or extended release embodiments accordingly.

Additional methods of formulating compositions known to the skilled artisan, for example, are described in the *Physicians Desk Reference*, 62nd edition. Oradell, N.J.: Medical Economics Co., 2008; Goodman & Gilman's *The Pharmacological Basis of Therapeutics*, Eleventh Edition. McGraw-Hill, 2005; *Remington: The Science and Practice of Pharmacy*, 20th Edition. Baltimore, Md.: Lippincott Williams & Wilkins, 2000; and *The Merck Index*, Fourteenth Edition. Whitehouse Station, N.J.: Merck Research Laboratories, 2006; each of which is hereby incorporated by reference in relevant parts.

H. Administration

In particular embodiments, a method of treating a subject with a hematological malignancy is contemplated comprising administering to the subject a JAK2 inhibitor and a glucocorticoid. In certain embodiments, the methods contemplated herein comprise administering a JAK2 inhibitor, thalidomide or a derivative thereof, and a glucocorticoid to a subject. Compositions contemplated herein may be administered as one or more solids, semi-solids, gels, or liquids, or combination thereof. For example, JAK2 inhibitors, thalidomide or derivatives thereof, glucocorticoids, and other pharmaceutically active agents may be individually formulated for intravenous administration in a liquid dosage form or for oral administration as a single tablet or capsule or as a combination of one or more tablets, capsules, or other dosage forms. The specific amount/dosage regimen will vary depending on the weight, gender, age, and health of the individual; the formulation, the biochemical nature, bioactivity, bioavailability and the side effects of the agents and the number and identity of the agents in the complete therapeutic regimen.

As used herein, the terms "administering," "administer," or "administration" refer to delivery of one or more compounds or compositions to a subject parenterally, enterally or topically. Illustrative examples of parenteral administration include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion. Illustrative examples of enteral administration include, but are not limited to oral, inhalation, intranasal, sublingual, and rectal administration. Illustrative examples of topical administration include, but are not limited to, transdermal and vaginal administration.

In particular embodiments, an agent or composition is administered parenterally, optionally by intravenous administration or oral administration to a subject.

In various embodiments, the development of suitable dosing and treatment regimens for using the particular compositions contemplated herein in a variety of treatment regimens including, e.g., oral, parenteral, intravenous, intranasal, and intramuscular administration and formulation, is well known in the art.

In particular embodiments, a JAK2 inhibitor, thalidomide or a derivative thereof, or glucocorticoid is administered orally to a subject. The agent can be administered to the subject at a dose in the range of about 1-100 mg, about 1-50 mg, about 50-100 mg, about 1-5 mg, about 5-10 mg, about 10-15 mg, about 15-20 mg, about 20-30 mg, about 30-40 mg, about 40-50 mg, about 50-60 mg, about 60-70 mg, about 70-80 mg, about 80-90 mg, or about 90-100 mg or more. In certain embodiments, the agent is administered in a dose of about 1 mg, about 2 mg, about 2.5 mg, about 3 mg, about 4 mg, about 5 mg, about 6 mg, about 7 mg, about 8 mg, about 9 mg, about 10 mg, about 15 mg, about 20 mg, about 25 mg, about 50 mg, or about 100 mg or more. In some embodiments of the invention, an oral dose of an agent is administered to the subject at least once in a treatment cycle, at least once in a 28 day treatment cycle, at least once a week, at least once every other day, at least once a day, or at least twice a day In particular embodiments, a JAK2 inhibitor, thalidomide or a derivative thereof, or glucocorticoid is administered intravenously. The agent can be administered intravenously at a dose of about 0-100 mg, about 1-50 mg, about 50-100 mg, about 1-10 mg, about 10-20 mg, about 20-30 mg, about 30-40 mg, about 40-50 mg, about 50-60 mg, about 60-70 mg, about 70-80 mg, about 80-90 mg, or about 90-100 mg or more. In certain embodiments, the intravenous dose of agent is about one mg, about two mg, about three mg, about four mg, about five mg, about six mg, about seven mg, about eight mg, about nine mg, about ten mg, about 15 mg, about 20 mg, about 25 mg, about 30 mg, about 35 mg, about 40 mg, about 45 mg, about 50 mg, about 60 mg, about 70 mg, about 80 mg, about 90 mg, or about 100 mg or more. Doses of agents can be delivered intravenously in any pharmaceutically suitable vehicles for injection or infusion known in the art.

In some embodiments, a JAK2 inhibitor, thalidomide or a derivative thereof, and a glucocorticoid are each administered at least once during a treatment cycle. In some embodiments, a JAK2 inhibitor, thalidomide or a derivative thereof, and a glucocorticoid are administered to the subject on the same days. In some embodiments, a JAK2 inhibitor, thalidomide or a derivative thereof, and a glucocorticoid are administered to the subject on the different days. In some embodiments, a JAK2 inhibitor, thalidomide or a derivative thereof, and a glucocorticoid are administered to the subject on the same days and on different days according to treatment schedules.

In particular embodiments, an agent is administered to the subject over one or more treatment cycles. A treatment cycle can be at least two, at least three, at least four, at least five, at least six, at least seven, at least 14, at least 21, at least 28, at least 48, or at least 96 days or more. In one embodiment, a treatment cycle is 28 days. In certain embodiments, the agents are administered over the same treatment cycle or over different treatment cycles. In various embodiments, the treatment cycle is determined by a health care professional based on conditions and needs of the subject.

In some embodiments, an agent is administered on at least one day, at least two days, at least three days, at least four days, at least five days, at least six days, at least seven days, at least eight days, at least nine days, at least ten days, at least eleven days, at least twelve days, at least 13 days, at least 14 days, at least 21 days, or all 28 days of a 28 day treatment cycle. In particular embodiments, an agent is administered to a subject once a day. In other particular embodiments, an agent is administered twice a day. In certain embodiments, an agent is administered more than twice a day.

The number of times a composition is administered to a subject in need thereof depends on the discretion of a medical professional, the disorder, the severity of the disorder, and the subject's response to the formulation. In some embodiments, a composition disclosed herein is administered once to a subject in need thereof with a mild acute condition. In some embodiments, a composition disclosed herein is administered more than once to a subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may be administered continuously; or, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

I. Methods

In various embodiments, methods of treating, preventing, or ameliorating at least one symptom of a hematological malignancy are provided. Illustrative examples of hematological malignancies suitable for treatment with the compositions and methods contemplated herein include, but are not limited to multiple myeloma, leukemia, or lymphoma. Leukemias can include, but are not limited to, acute lymphoblastic leukemia, acute myelogenous leukemia, chronic lymphocytic leukemia, chronic myelogenous leukemia, acute monocytic leukemia, and myeloproliferative disorders. Lymphomas can include, but are not limited to, Hodgkin's lymphomas, such as nodular sclerosis Hodgkin's lymphoma, mixed cellularity subtype Hodgkin's lymphoma, Lymphocyte rich Hodgkin's lymphoma, and lymphocyte depleted Hodgkin's lymphoma; and non-Hodgkin's lymphoma, such as diffuse large B-cell lymphoma, primary mediastinal B-cell lymphoma, follicular lymphoma, chronic lymphocytic leukemia, mantle cell lymphoma, marginal zone B-cell lymphomas, Burkitt lymphoma, lymphoplasmacytic lymphoma, primary central nervous system lymphoma, T-cell lymphomas, and macroglobulinemia. Myeloma includes all plasma cell dyscrasias including multiple myeloma and primary amyloidosis, but are not limited to multiple myeloma and amyloidosis. Without wishing to be bound to any particular theory, it is contemplated that the treatment of a hematological malignancy with the compositions contemplated herein offer patients with relapsed or refractory cancers an improved therapeutic outcome and increased chance of long-term survival.

In various embodiments, the methods contemplated herein comprise administration of a JAK2 inhibitor and one or more other pharmaceutically acceptable agents to synergistically treat a hematological malignancy. In one embodiment, a JAK2 inhibitor is combined with a glucocorticoid to synergistically treat a hematological malignancy. In a particular embodiment, a JAK2 inhibitor is combined with a glucocorticoid and thalidomide or a derivative thereof to synergistically treat a hematological malignancy.

In particular embodiments, methods of preventing, ameliorating one or more symptoms of, or treating a subject having multiple myeloma are provided. In particular embodiments, the methods comprise administering a JAK2 inhibitor and one or more other pharmaceutically acceptable agents. In one embodiment, a subject having multiple myeloma is administered a JAK2 inhibitor and a glucocorticoid. In a certain embodiment, a subject having multiple myeloma is administered a JAK2 inhibitor combined with a glucocorticoid and thalidomide or a derivative thereof. In certain embodiments, methods of preventing, ameliorating one or more symptoms of, or treating a subject having a relapsed hematological malignancy, e.g, multiple myeloma, are provided. In one embodiment, a method of treating a subject with a relapsed hematological malignancy comprises administering a JAK2 inhibitor and one or more other pharmaceutically acceptable agents. In another embodiment, a subject having a relapsed hematological malignancy is administered a JAK2 inhibitor and a glucocorticoid. In a certain embodiment, a subject having relapsed hematological malignancy is administered a JAK2 inhibitor combined with a glucocorticoid and thalidomide or a derivative thereof.

In some embodiments, methods of preventing, ameliorating one or more symptoms of, or treating a subject having a hematological malignancy that is refractory to one or more prior cancer treatments are provided. In one embodiment, a method of treating a subject with a refractory hematological malignancy comprises administering a JAK2 inhibitor and one or more other pharmaceutically acceptable agents. In another embodiment, a subject having a refractory hematological malignancy is administered a JAK2 inhibitor and a glucocorticoid. In a certain embodiment, a subject having refractory hematological malignancy is administered a JAK2 inhibitor combined with a glucocorticoid and thalidomide or a derivative thereof.

In particular embodiments, the relapsed or refractory malignancy was previously treated with one or more of a chemotherapeutic agent, e.g., doxorubicin; a proteasome inhibitor, e.g., bortezomib, carfilzomib; thalidomide or a derivative thereof, e.g., pomalidomide, lenalidomide; a glucocorticoid, e.g., dexamethasone, methylprednisone, methylprednisolone, or prednisone; or other agents including but not limited to alkylating agents, anthracyclines, taxanes, histone deacetylase inhibitors, topoisomerase inhibitors, kinase inhibitors, monoclonal antibodies, nucleotide analogs and precursor analogs, peptide antibiotics, retinoids, and vinca alkaloids. In one embodiment, the relapsed or refractory malignancy was previously treated with thalidomide or a derivative thereof and a glucocorticoid. In another embodiment, the relapsed or refractory malignancy was not previously treated with a JAK2 inhibitor, thalidomide or a derivative thereof, and a glucocorticoid.

In particular embodiments, a subject having a hematological malignancy is administered a JAK2 inhibitor selected from the group consisting of: ruxolitinib, fedratinib, baricitinib, Pacritinib, AZD1480, XL019, LY2784544, BMS-911543, XL019, NS-018, CYT387, atiprimod dihydrochloride, CP 690550, Cucurbitacin I, 1,2,3,4,5,6-Hexabromocyclohexane, Lestaurtinib, NSC 33994, and SD 1008; a glucocorticoid; and optionally thalidomide or a derivative thereof.

In certain embodiments, a subject having a hematological malignancy is administered a JAK2 inhibitor; a glucocorticoid selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol; and optionally thalidomide or a derivative thereof.

In various embodiments, a subject having a hematological malignancy is administered a JAK2 inhibitor; a glucocorticoid; and thalidomide or a derivative thereof selected from the group consisting of lenalidomide, pomalidomide, linomide, CC-1088, CDC-501, and CDC-801.

In particular embodiments, a subject having a hematological malignancy is administered a JAK2 inhibitor selected from the group consisting of ruxolitinib and CP-690550; a glucocorticoid selected from the group consisting of dexamethasone, methylprednisone, methylprednisolone, and prednisone; and thalidomide or a derivative thereof selected from the group consisting of thalidomide, lenalidomide, pomalidomide, and linomide. It is understood that any agent from each class can be combined with any other agent from a different class. In additional embodiments, a subject is also administered one or more additional pharmaceutically active agents.

In one embodiment, a subject having a hematological malignancy is administered ruxolitinib, methylprednisone or methylprednisolone, and lenalidomide.

In one embodiment, a subject having a hematological malignancy is administered CP-690550, methylprednisone or methylprednisolone, and lenalidomide.

All publications, patent applications, and issued patents cited in this specification are herein incorporated by reference as if each individual publication, patent application, or issued patent were specifically and individually indicated to be incorporated by reference in its entirety.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Multiple Myeloma Cell Lines Treated with Ruxolitinib In Vitro

This example demonstrates that ruxolitinib, a JAK2 inhibitor, reduced viability of cultured multiple myeloma tumor cell lines Inhibitory concentration (IC) curves of ruxolitinib were determined using the multiple myeloma tumor cell lines U266, MM1s and RPMI8226. Cells were seeded in 96-well plates at a concentration of $10^5$ cells/100 µl/well and incubated for 24 hours. Cells were then treated with either control or ruxolitinib at several concentrations for 48 hours. After 48 h, cell viability was assessed with the MTS assay. Ruxolitinib induced a concentration-dependent inhibition of viability in U266 (FIG. 1), RPMI8226 (FIG. 1B), and MM1s (FIG. 1C) multiple myeloma cell lines.

Example 2

Synergy of Ruxolitinib, Lenalidomide and Dexamethasone In Vitro

In vitro proliferation experiments were performed with the JAK2 inhibitor ruxolitinib in combination with lenalidomide or dexamethasone using the Chou-Talalay method. Different concentrations of ruxolitinib were tested independently and in combination with a fixed concentration at the inhibitory concentration of 20%-30% ($IC_{20-30}$) of lenalidomide or dexamethasone.

Figure 2:
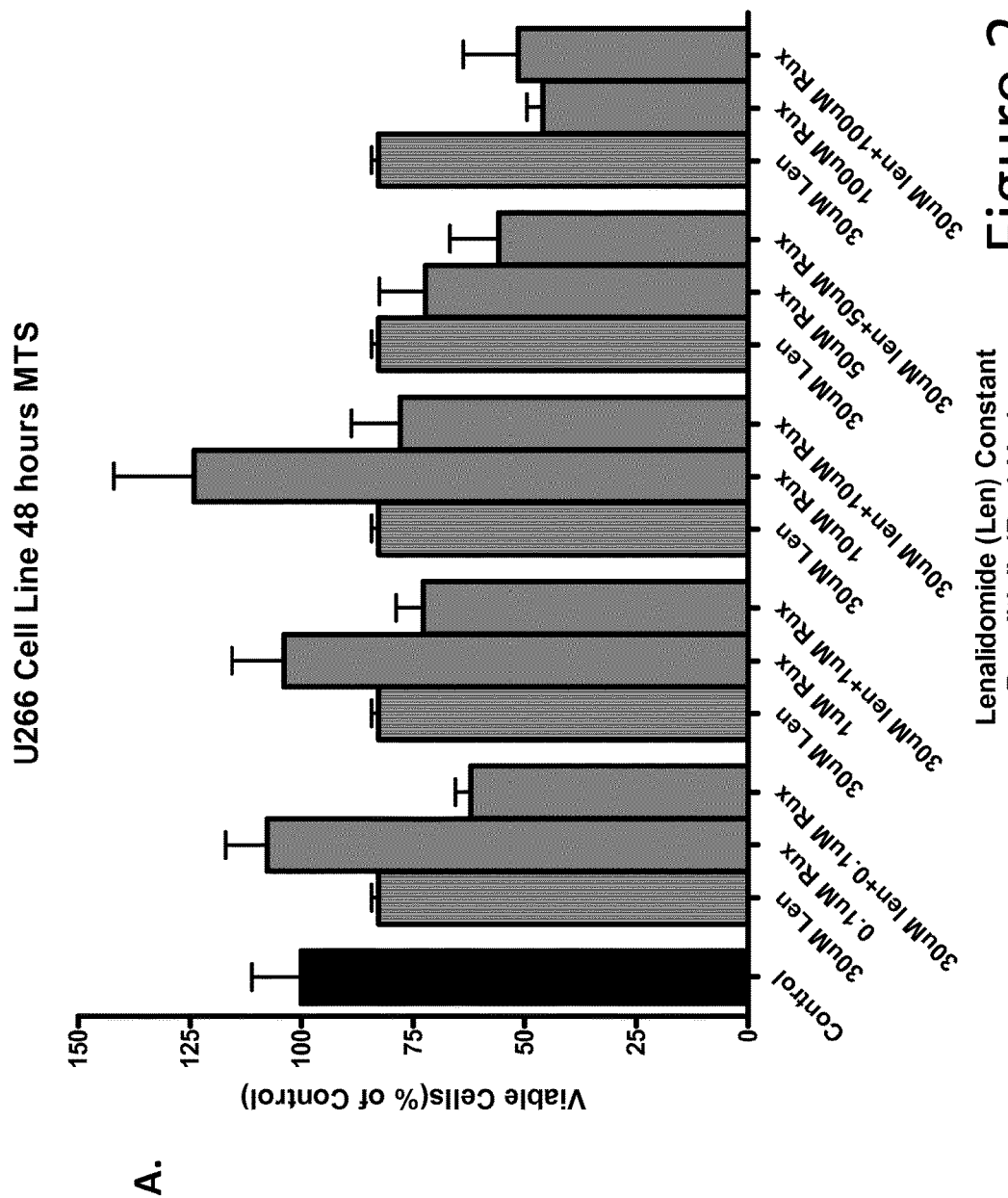
FIG. 2 shows a representative example of a multiple myeloma tumor cell viability assay of cells treated with a combination of a JAK2 inhibitor and a thalidomide derivative or glucocorticoid. The viability of U266 multiple myeloma tumor cells was assessed by cell proliferation MTS assay following 48 hours of incubation with A) vehicle, lenalidomide (Len), ruxolitinib (Rux), or both lenalidomide and ruxolitinib at the indicated concentrations, or B) vehicle, dexamethasone (Dex), ruxolitinib, or both dexamethasone and ruxolitinib at the indicated concentrations.
Figure 2:
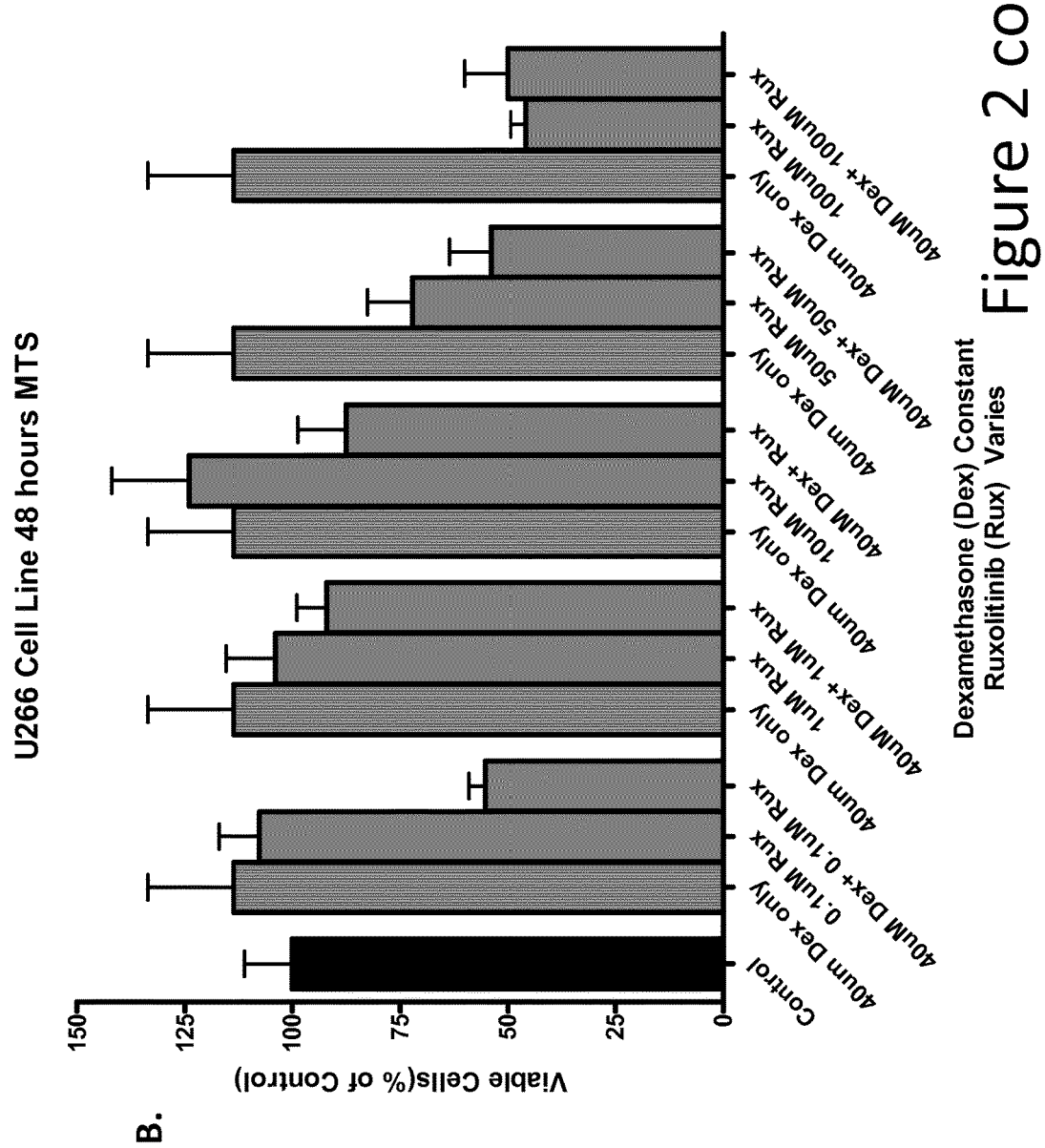
Figure 3:
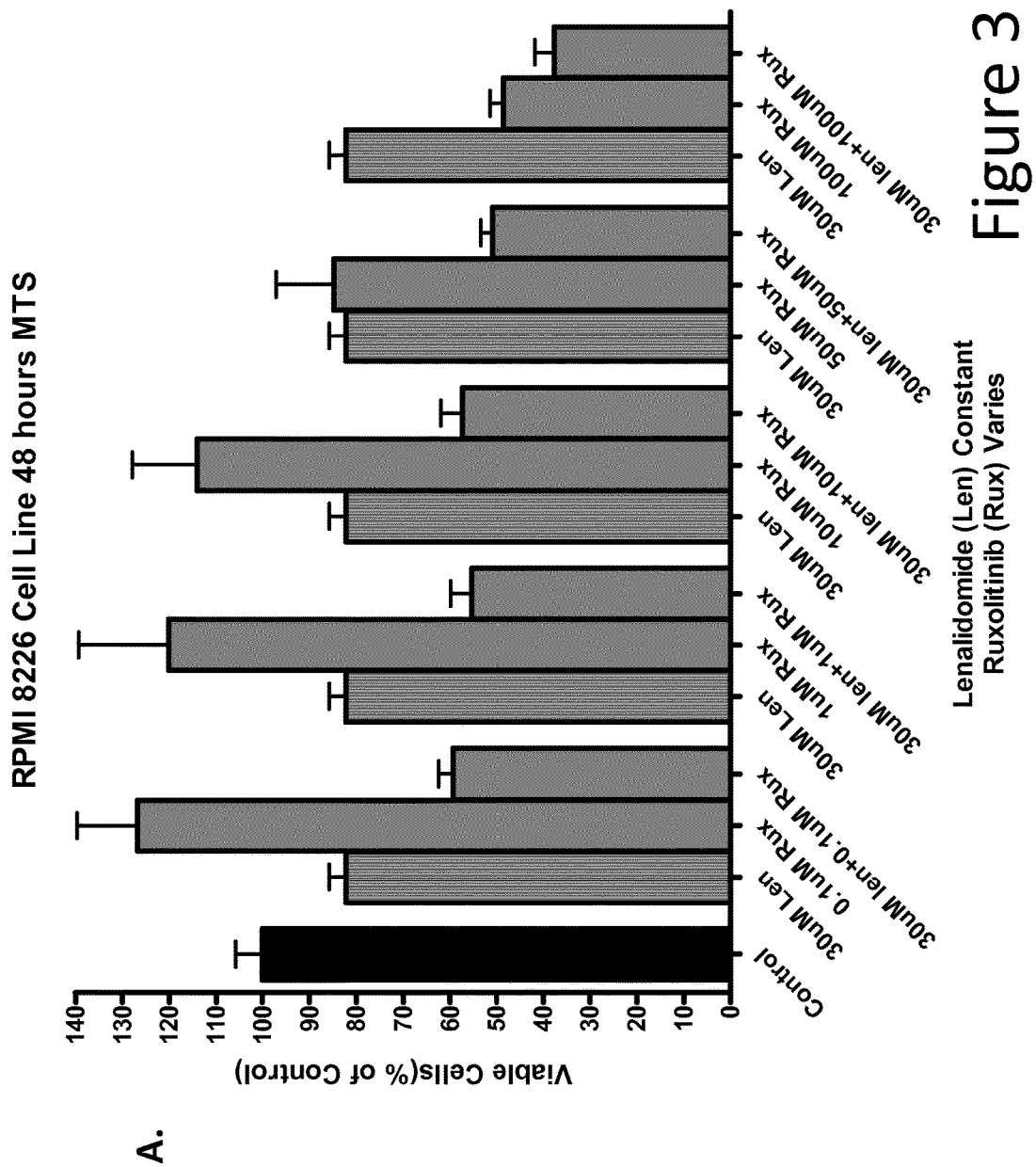
FIG. 3 shows a representative example of a multiple myeloma tumor cell viability assay of cells treated with a combination of a JAK2 inhibitor and a thalidomide derivative or glucocorticoid. The viability of RPMI8226 cells was assessed by cell proliferation MTS assay following 48 hours of incubation with A) vehicle, lenalidomide (Len), ruxolitinib (Rux), or both lenalidomide and ruxolitinib at the indicated concentrations or B) with vehicle, dexamethasone (Dex), ruxolitinib, or both dexamethasone and ruxolitinib at the indicated concentrations.
Figure 3:
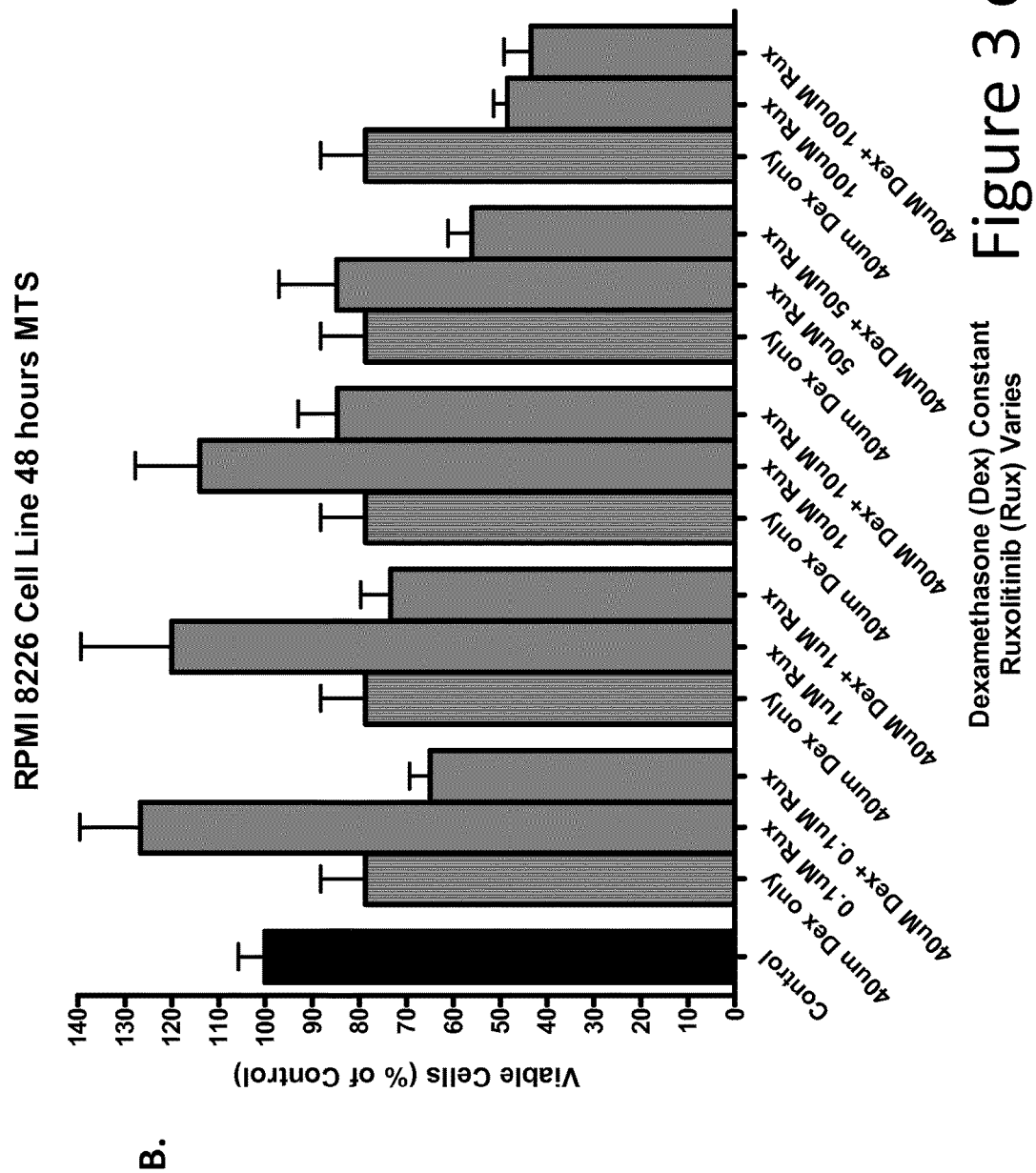

Viability of multiple myeloma cells treated with ruxolitinib and lenalidomide or dexamethasone was determined by MTS assay. Multiple myeloma cell lines were seeded as described above and incubated for 24 hours. In one experiment, U266 cells were treated with vehicle, lenalidomide (30 µM), increasing concentrations of ruxolitinib (0.1 µM to 100 µM), or combined treatment lenalidomide and ruxolitinib for 48 hours (FIG. 2A). In another experiment, U266 cells were treated with vehicle, dexamethasone (40 µM), increasing concentrations of ruxolitinib (0.1 µM to 100 µM), or combined treatment with dexamethasone and ruxolitinib for 48 hours (FIG. 2B). The experiments were repeated with RPMI8226 cells (FIGS. 3A and 3B).

Figure 4:
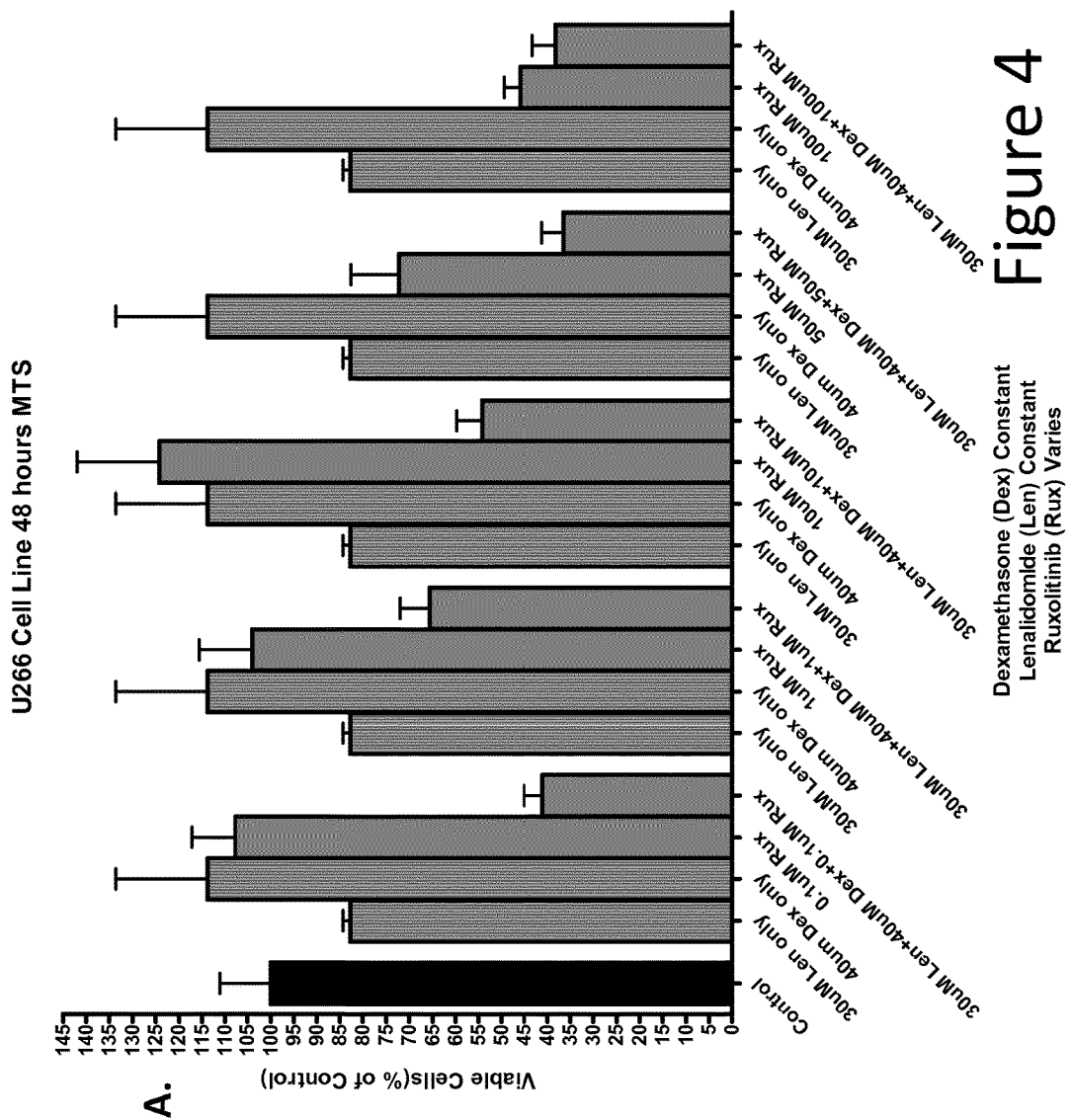
FIG. 4 shows a representative example of a multiple myeloma tumor cell viability assay of cells treated with a combination of a JAK2 inhibitor, a thalidomide derivative, and a glucocorticoid. The viability of A) U266 multiple myeloma tumor cells, or B) RPMI8226 cells was assessed by cell proliferation MTS assay. Cells were incubated with vehicle, lenalidomide (Len), dexamethasone (Dex), ruxolitinib (Rux), or all three agents for 48 hours at the indicated concentrations.
Figure 4:
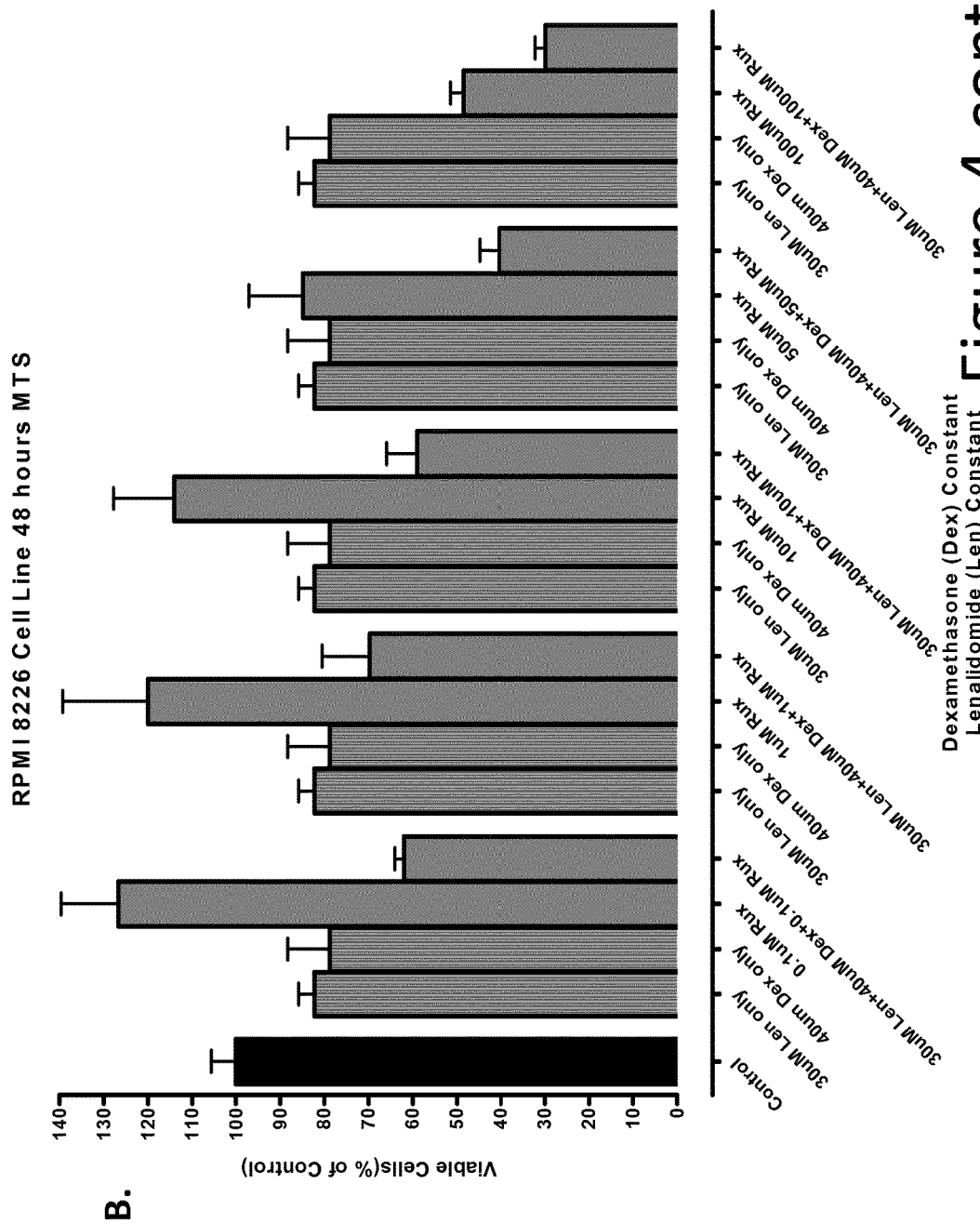

The U266 cells or RPMI8226 cells were then treated with vehicle, lenalidomide (30 µM), dexamethasone (40 µM), increasing concentrations of ruxolitinib (0.1 µM to 100 µM), or combined treatment with lenalidomide, ruxolitinib and dexamethasone for 48 hours (FIGS. 4A and 4B). In another experiment, U266 cells or RPMI8226 cells were incubated with a vehicle control and increasing concentrations of ruxolitinib (0.1 µM to 100 µM) combined with dexamethasone, with lenalidomide, or with dexamethasone and lenalidomide (FIGS. 5A and 5B).

Figure 5:
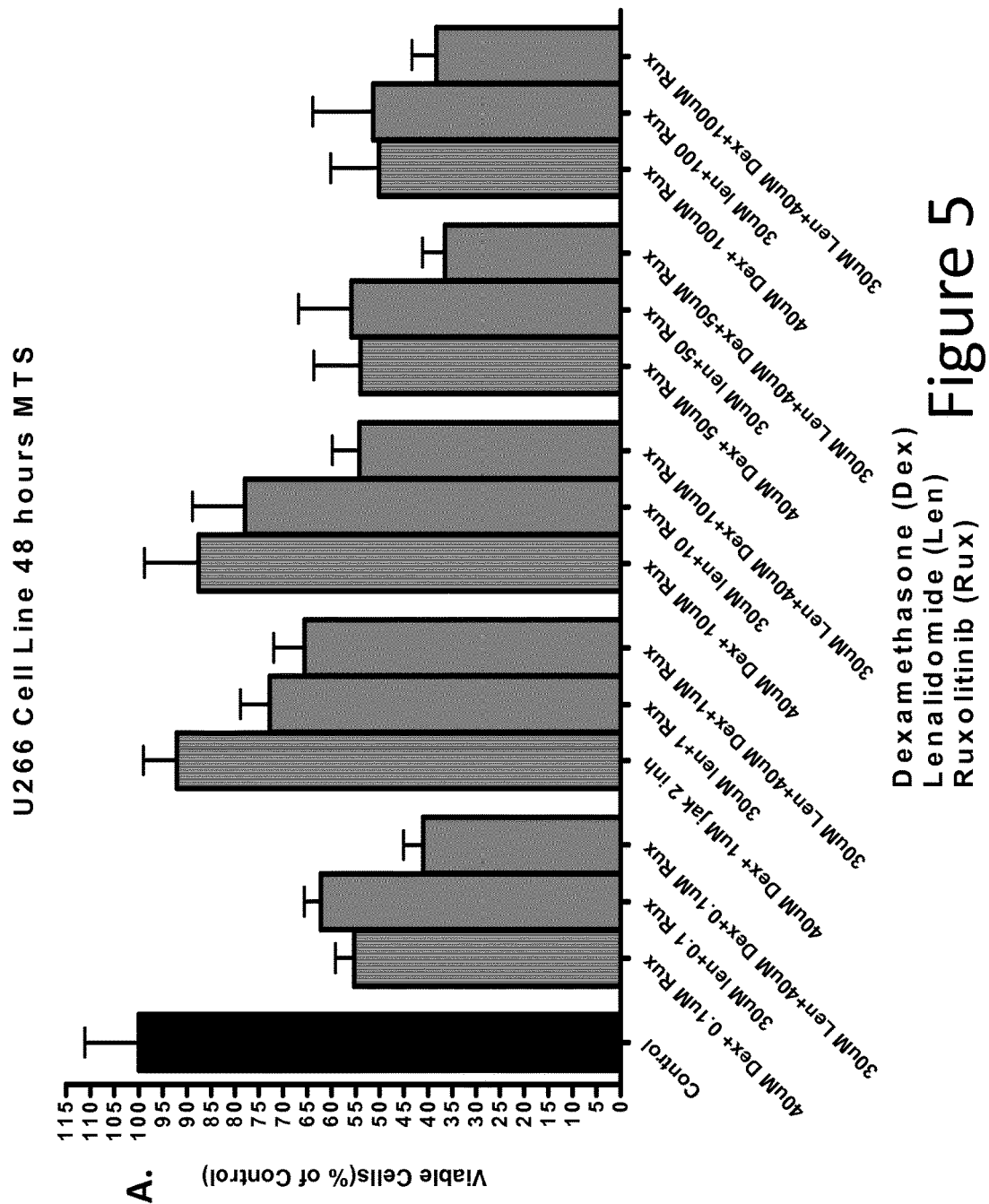
FIG. 5 shows a representative example of a multiple myeloma tumor cell viability assay of cells treated with a combination of a JAK2 inhibitor, a thalidomide derivative, and a glucocorticoid. The viability of A) U266 multiple myeloma tumor cells, or B) RPMI8226 cells was assessed using the cell proliferation MTS assay. Cells were incubated with vehicle (black bar), ruxolitinib (Rux) combined with dexamethasone (Dex), ruxolitinib combined with lenalidomide (Len), or all three agents for 48 hours at the indicated concentrations.
Figure 5:
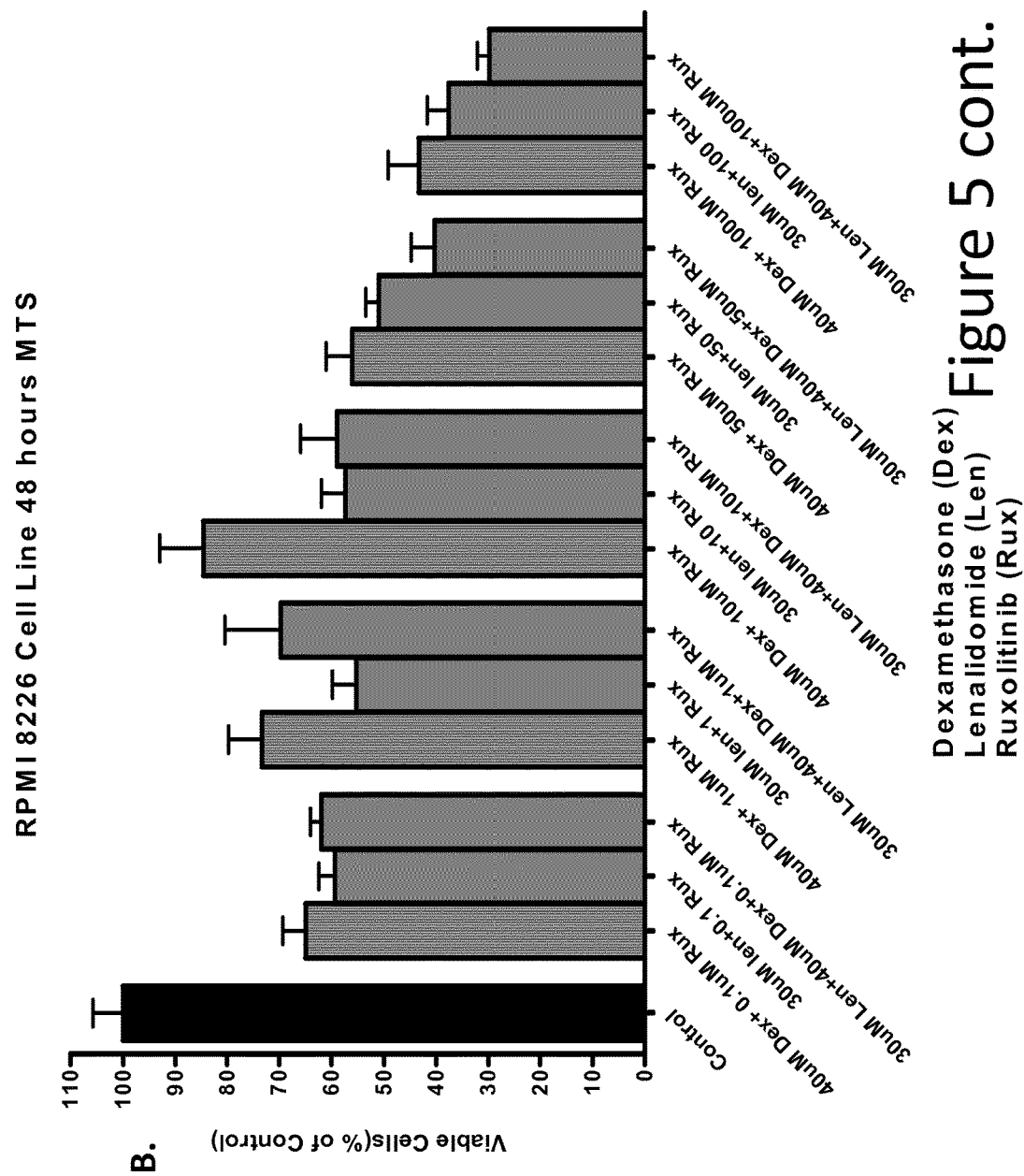

The results demonstrated that combination of ruxolitinib, lenalidomide and dexamethasone synergistically enhanced the cytotoxic effects in the U266 and RPMI8226 multiple myeloma cell lines (see FIGS. 4B and 5A). Moreover, the cytotoxic effects of ruxolitinib, lenalidomide and dexamethasone were greater than the ruxolitinib in combination with either lenalidomide or dexamethasone in U266 cells (FIG. 5A) or RPMI8226 cells (FIG. 5B).

Example 3

Primary Cells Treated with Ruxolitinib, Lenalidomide, and Dexamethasone

Figure 6:
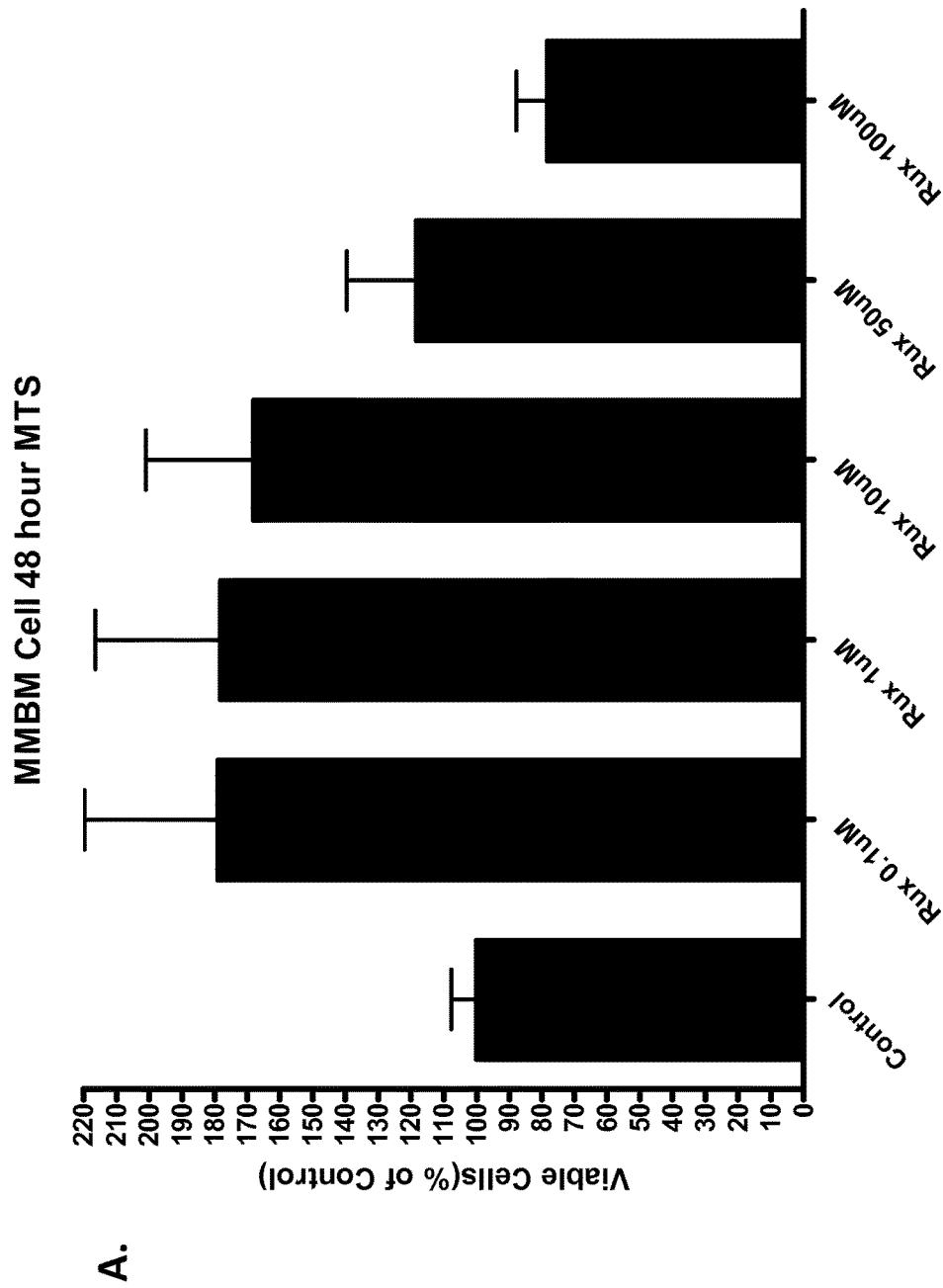
FIG. 6 shows a representative example of a multiple myeloma tumor cell viability assay of primary cells treated with a JAK2 inhibitor. The viability of primary multiple myeloma bone marrow tumor cells was assessed using the cell proliferation MTS assay following 48 hours of incubation with A) the indicated concentrations of ruxolitinib (Rux) or B) vehicle, lenalidomide (Len), dexamethasone (Dex), ruxolitinib (Rux), or all three agents for 48 hours at the indicated concentrations.
Figure 6:
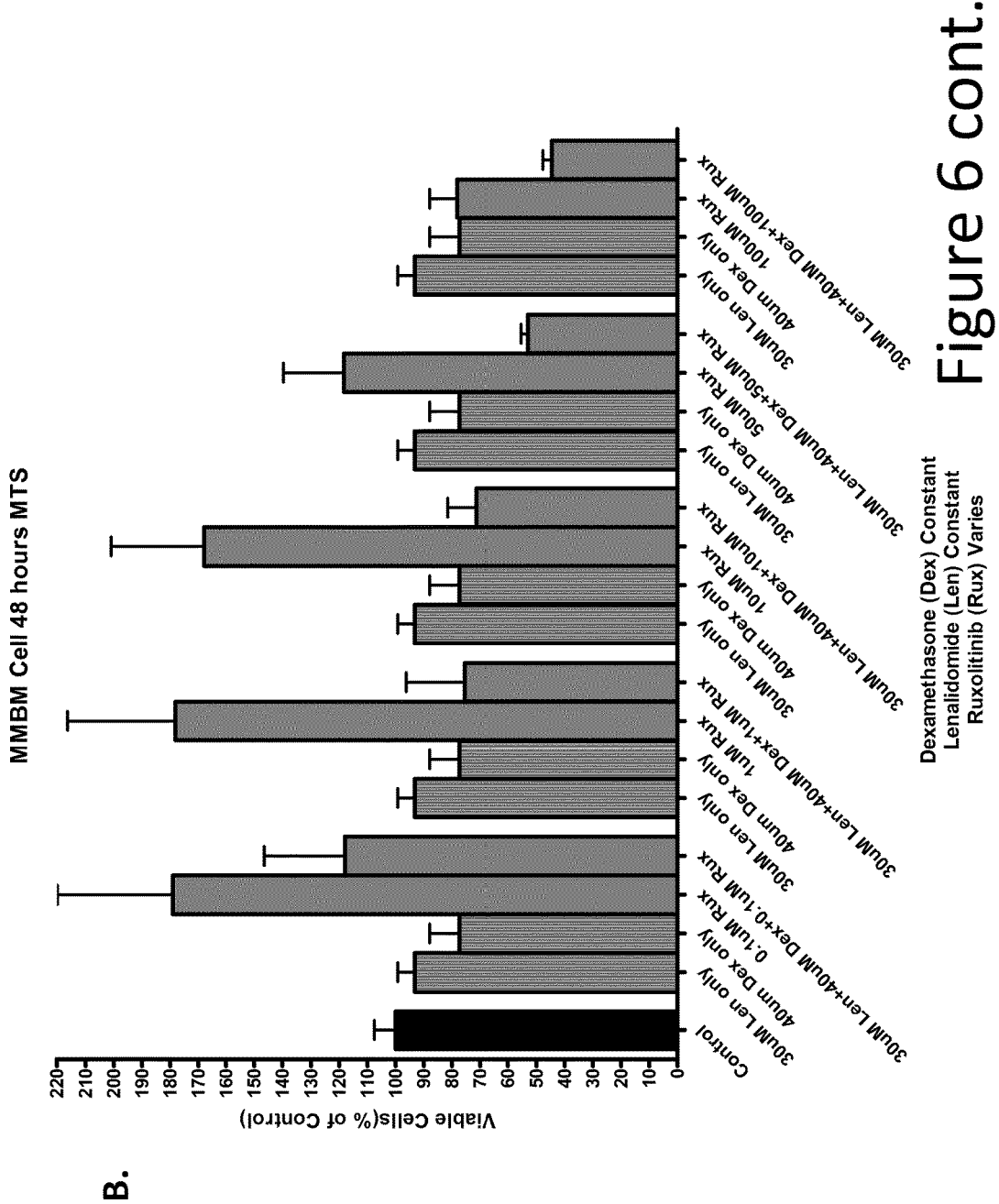

In vitro proliferation experiments were performed in primary multiple myeloma tumor cells with the JAK-2 inhibitor ruxolitinib in combination with lenalidomide or dexamethasone using the Chou-Talalay method. Multiple myeloma bone marrow mononuclear (MMBM) cells were collected from multiple myeloma patients and plated to generate primary multiple myeloma cell cultures. In one experiment, the IC curve of ruxolitinib in primary MMBM cells was determined. Primary MMBM cells were incubated with ruxolitinib at several concentrations for 48 hours. After 48 hours, cell viability was assessed with an MTS assay (FIG. 6A). Ruxolitinib alone only mildly inhibited the viability of primary multiple myeloma cells.

In another experiment, primary cells were incubated with a vehicle control, a fixed concentration of lenalidomide (30 µM), a fixed concentration of dexamethasone (40 µM), increasing concentrations of ruxolitinib (0.1 µM to 100 µM), or combined exposure to lenalidomide, ruxolitinib and dexamethasone for 48 hours. After 48 hours, cell viability was assessed with an MTS assay (FIG. 6B). The results demonstrated that the combination of ruxolitinib, lenalidomide and dexamethasone synergistically enhanced the cytotoxic effects in primary multiple myeloma cells.

Example 4

Multiple Myeloma Cell Lines Treated with CP-690550 In Vitro

In vitro experiments were performed to determine synergy of the JAK2 inhibitor tofacitinib citrate (CP-690550) in combination with lenalidomide or dexamethasone using the Chou-Talalay method. As with experiments testing the JAK2 inhibitor ruxolitinib, experiments were designed testing different concentrations of CP-690550 independently and in combination with lenalidomide and dexamethasone with fixed concentrations at $IC_{20-30}$.

Viability in the presence of CP-690550 alone or in the presence of lenalidomide and dexamethasone was determined with an MTS assay. Cells from multiple myeloma cell lines were seeded as described above. U266 cells were incubated with a vehicle control, a fixed concentration of lenalidomide (30 µM), a fixed concentration of dexamethasone (40 µM), increasing concentrations of CP-690550 (0.1 µM to 100 µM), or combined exposure to lenalidomide, CP-690550 and dexamethasone for 48 hours (see FIG. 7a). The combination of CP-690550, lenalidomide, and dexamethasone significantly enhanced cytotoxicity on U266 cells compared to either of the drugs administered alone.

Figure 7:
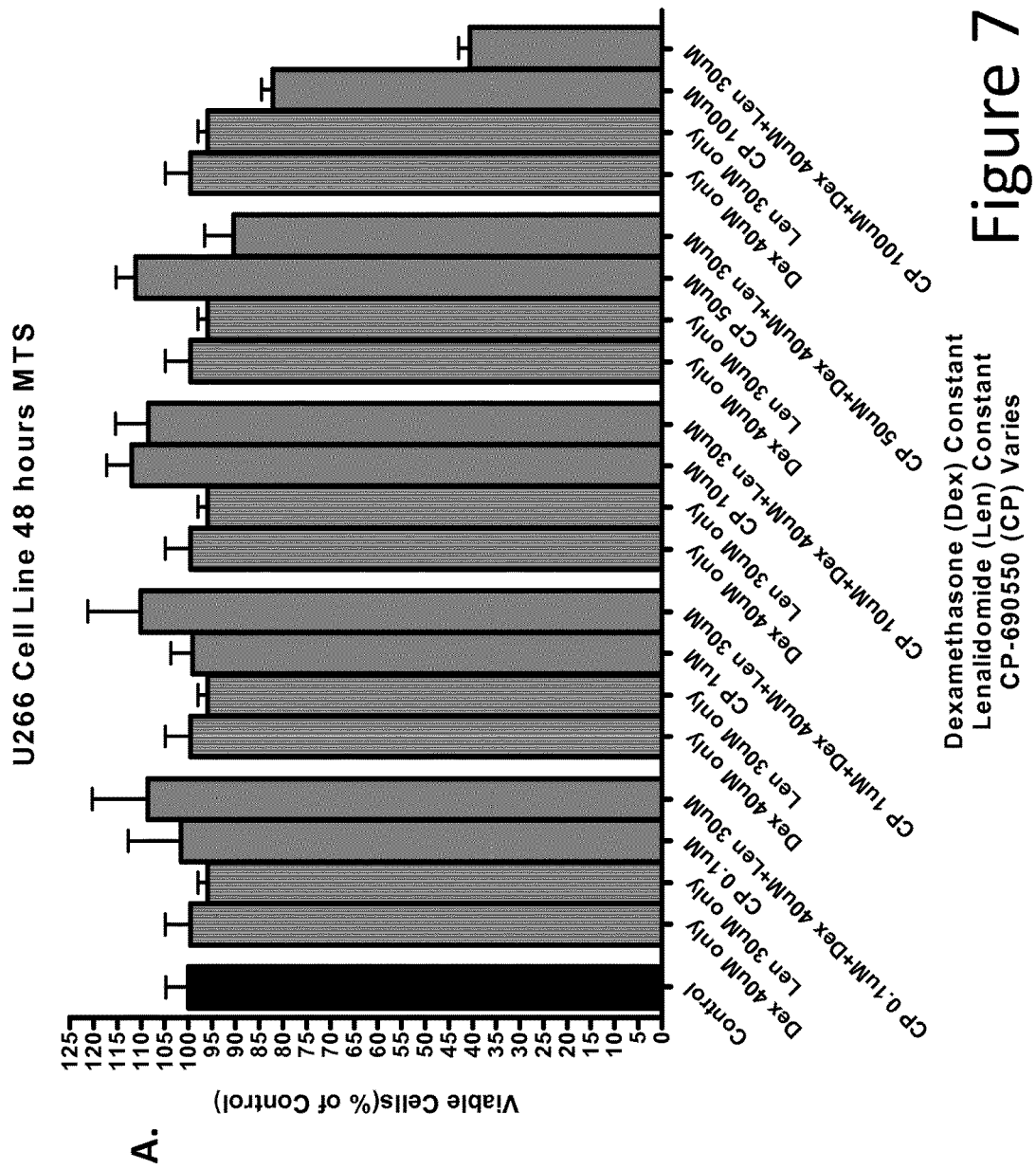
FIG. 7 shows a representative example of a multiple myeloma tumor cell viability assay of cells treated with a combination of a JAK2 inhibitor, a thalidomide derivative, and a glucocorticoid. The viability of A) U266 multiple myeloma tumor cells, or B) U266 cells was assessed with the cell proliferation MTS assay for comparing two drug combinations to three combinations. Cells were incubated with vehicle, dexamethasone (Dex), lenalidomide (Len), CP-690550 (CP), or combination agents for 48 hours at the indicated concentrations.
Figure 7:
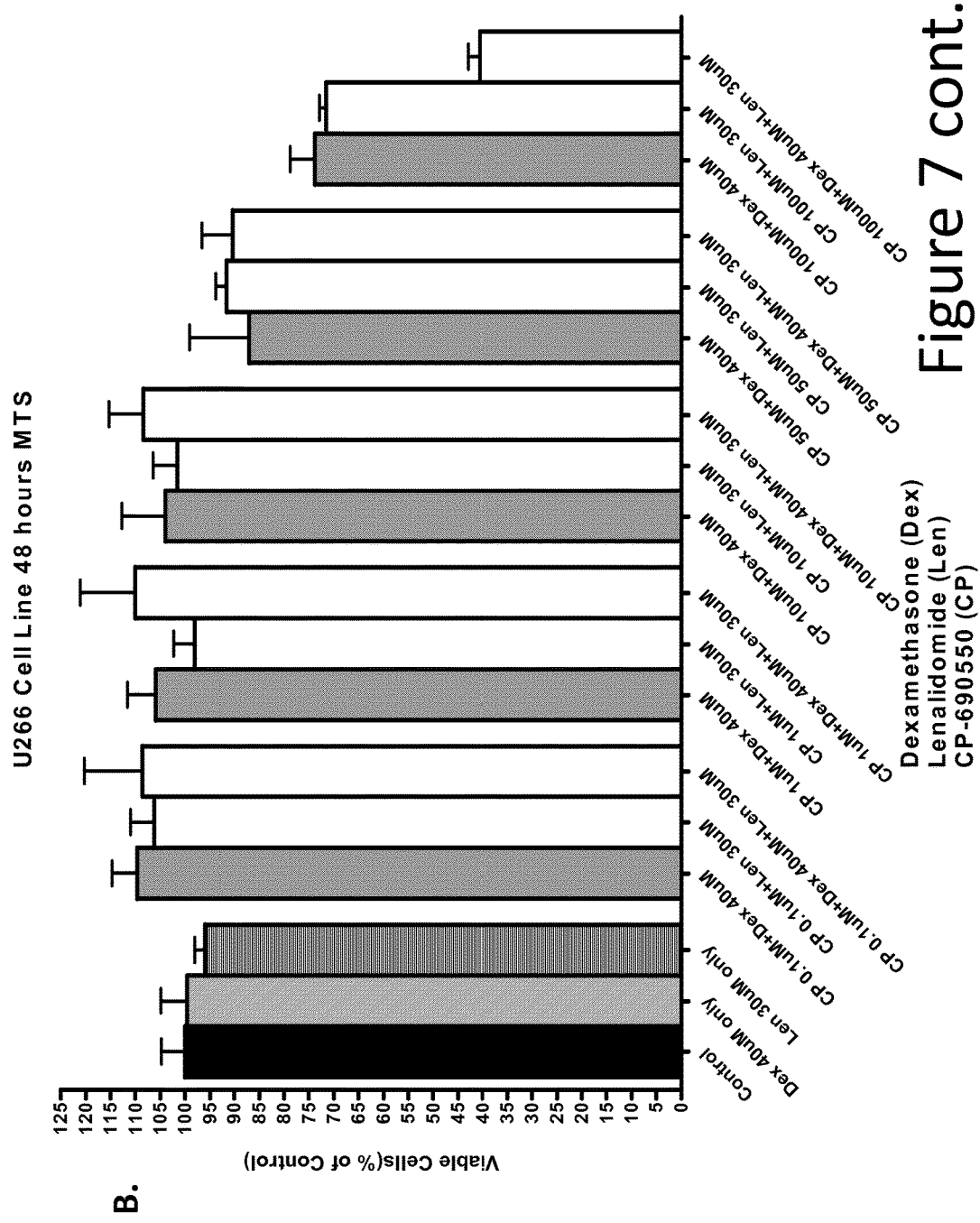

In another experiment, U266 cells were incubated with a vehicle control and increasing concentrations of CP-690550 (0.1 µM to 100 µM) combined with dexamethasone, with lenalidomide, or with dexamethasone and lenalidomide for 48 hours (see FIG. 7B). Cell viability was then assessed with an MTS assay. The CP-690550 combinations with either lenalidomide or dexamethasone reduced tumor cell growth. However, when CP-690550 was combined with lenalidomide and dexamethasone, the cytotoxic effects of CP-690550 were significantly enhanced. The results demonstrated that combination of CP-690550, lenalidomide and dexamethasone synergistically enhanced the cytotoxic effects in primary multiple myeloma cells.

Example 5

Treatments of Multiple Myeloma Tumors In Vivo

The combination of the JAK2 inhibitor ruxolitinib with lenalidomide and dexamethasone was tested on human multiple myeloma tumors in vivo. The anti-multiple myeloma effects of ruxolitinib were evaluated with mice bearing either LAGκ-1A (bortezomib- and melphalan-sensitive) or LAGκ-2 (bortezomib- and melphalan-resistant) tumors, both of which were originally derived from bone marrow biopsies from multiple myeloma patients. These tumors closely resemble human multiple myeloma and have been passaged through multiple generations of mice with consistent growth and chemoresistance patterns.

Figure 8:
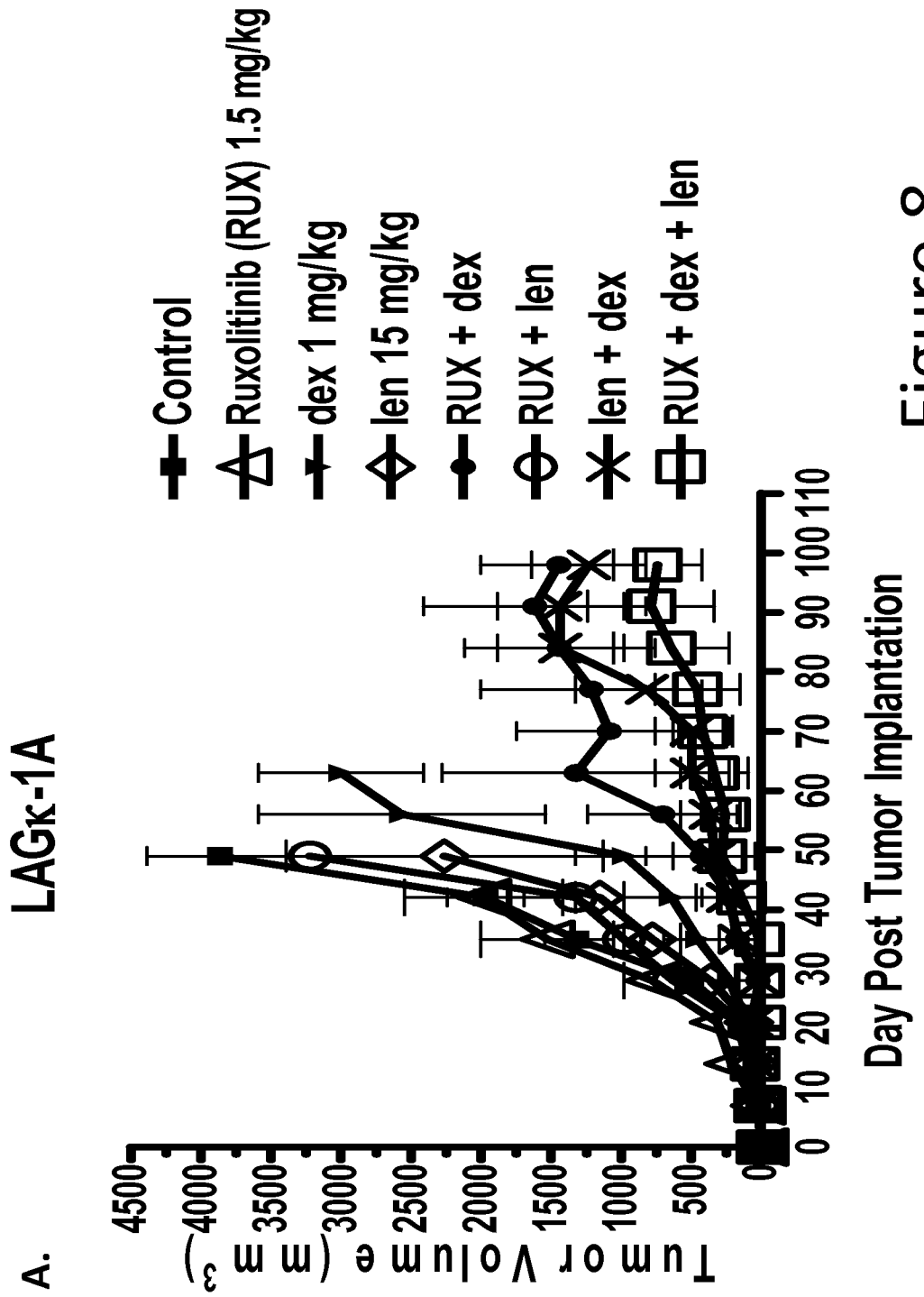
FIG. 8 shows a representative example of human multiple myeloma tumors that were implanted into severe combined immunodeficient mice and treated with a combination of a JAK2 inhibitor, a thalidomide derivative, and a glucocorticoid in vivo. Mice were implanted with A) human LAGκ-1A tumors or B) human LAGκ-2 tumors. Fourteen days after implantation, mice received intraperitoneal injections of vehicle control or ruxolitinib (1.5 mg/kg) twice daily, intraperitoneal injections of dexamethasone (1 mg/kg for LAGκ-1A and 1.5 mg/kg for LAGκ-2) daily, lenalidomide 15 mg/kg daily delivered by oral gavage, or combinations of ruxolitinib and dexamethasone, ruxolitinib and lenalidomide, dexamethasone and lenalidomide, or all three agents.
Figure 8:
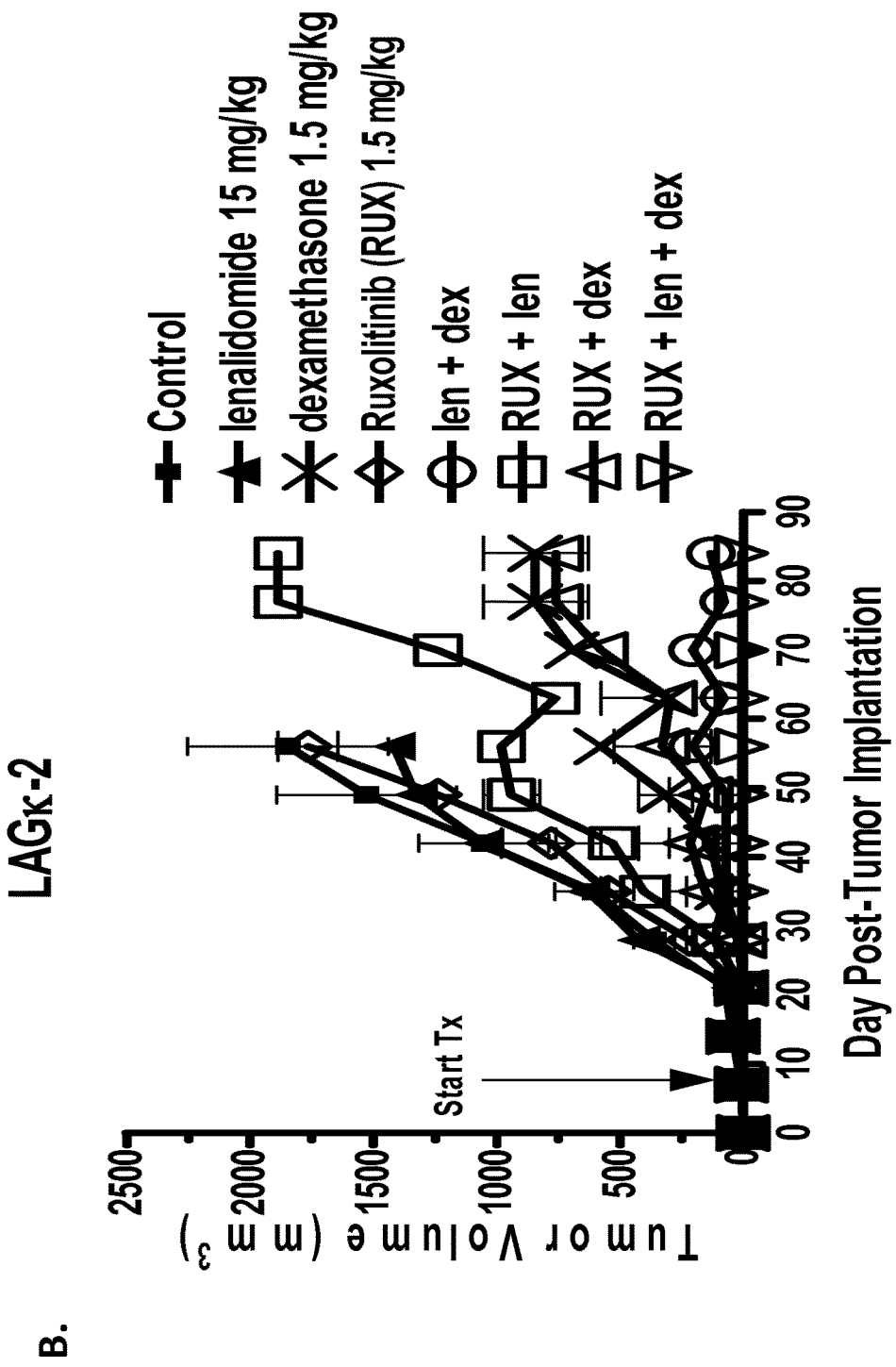

Following intramuscular implantation of LAGκ-1A tumor tissue, mice underwent treatment with vehicle control, ruxolitinib, dexamethasone, lenalidomide, ruxolitinib and dexamethasone, ruxolitinib and lenalidomide, dexamethasone and lenalidomide, or ruxolitinib with lenalidomide and dexamethasone (see FIG. 8A). Ruxolitinib was administered via injection at 1.5 mg/kg i.p., twice daily; dexamethasone was administered at 1 mg/kg i.p., once daily, and lenalidomide was administered via oral gavage at 15 mg/kg, once daily. When ruxolitinib, lenalidomide, or dexamethasone was administered individually, LAGκ-1A tumor growth was not inhibited compared to control. The combined treatment of ruxolitinib and lenalidomide also did not inhibit LAGκ-1A tumor growth compared to control conditions. However, combined treatment with ruxolitinib, lenalidomide, and dexamethasone synergistically inhibited LAGκ-1A tumor growth compared to control treatment.

In another experiment, mice received an intramuscular implantation of LAGκ-2 tumor tissue, and then underwent treatment with vehicle control, ruxolitinib, dexamethasone, lenalidomide, ruxolitinib and dexamethasone, ruxolitinib and lenalidomide, dexamethasone and lenalidomide, or ruxolitinib with lenalidomide and dexamethasone, as described above (see FIG. 8B). Similar to the effects on LAGκ-1A tumors, when ruxolitinib, lenalidomide, or dexamethasone was administered individually, LAGκ-2 tumor growth was not inhibited compared to control. However, the combined treatment of ruxolitinib, lenalidomide, and dexamethasone synergistically inhibited LAGκ-2 tumor growth compared to control treatment.

Example 6

Case Study of Multiple Myeloma Patient

This example describes a case report of a patient who underwent treatment for multiple myeloma, including treatment that combined the JAK2 inhibitor ruxolitinib with lenalidomide and a glucocorticoid. The patient was born on May 21, 1924, and was 89 years old at the time of initial treatment.

Hematologic and Oncologic History

In 1980, the patient was diagnosed with a hypercoagulable state. In 1997, the patient was diagnosed with prostate cancer with no clinical evidence of disease (N.E.D.). In 1992, the patient was diagnosed with JAK2 positive polycythemia rubra vera (PRV). In 2011, the patient was diagnosed with monoclonal gammopathy of undetermined significance (MGUS), IgG lambda+. On Nov. 27, 2012, the patient was diagnosed with multiple myeloma, IgG lambda+.

Figure 9:
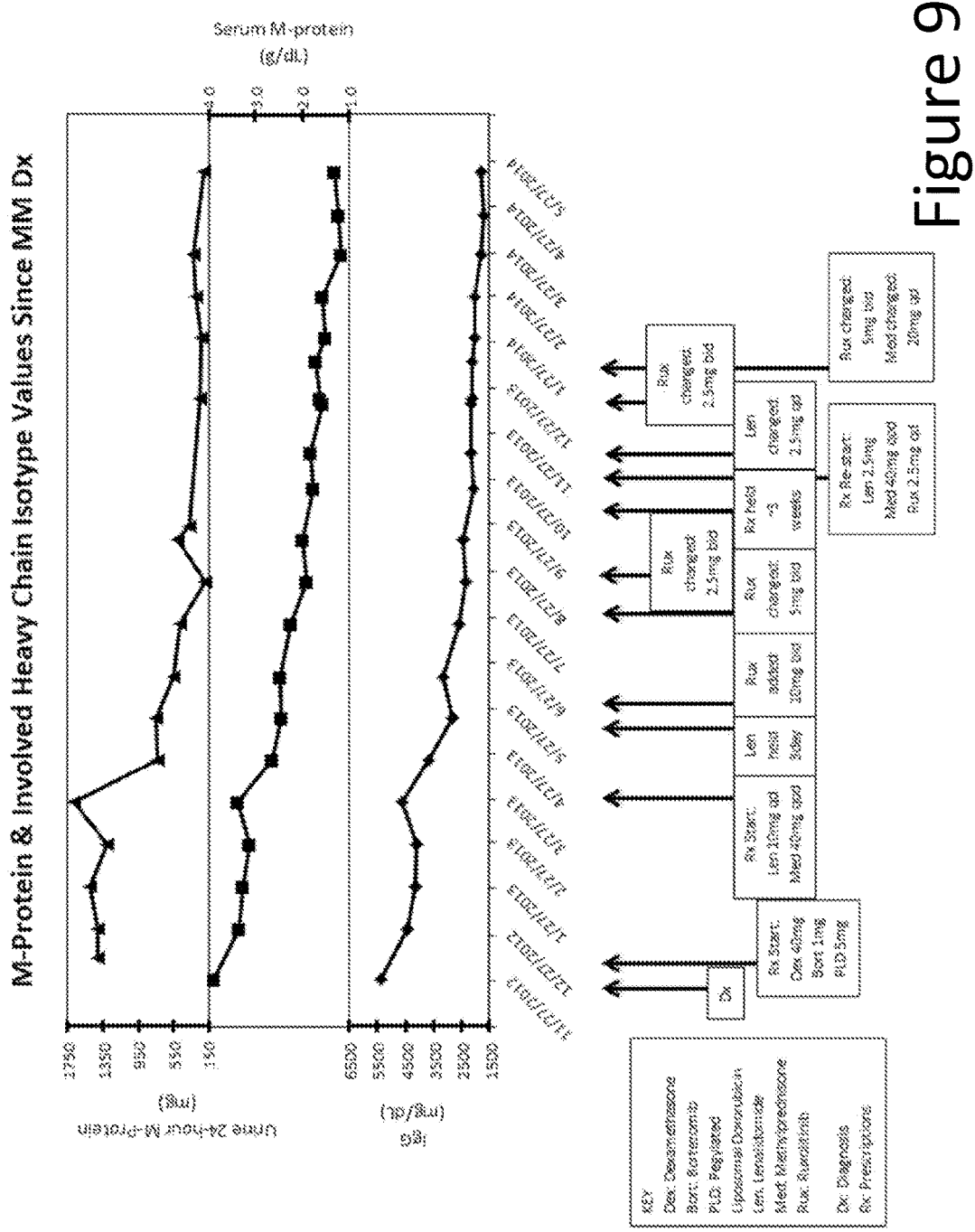
FIG. 9 shows a representative example of a patient's progress while undergoing treatments for multiple myeloma, including a combination of a JAK2 inhibitor, a thalidomide derivative, and a glucocorticoid. Measurements of M-protein and heavy chain isotype levels were taken from a patient beginning from the diagnosis of multiple myeloma. A graph shows levels of 24 hour M-protein in urine of the patient during treatment for multiple myeloma (top). A graph shows serum levels of serum M-protein during treatment (middle). A graph shows the serum IgG of the patient during the treatment (bottom). Changes in medication during the treatment are indicated along the X-axis with arrows.
Figure 10:
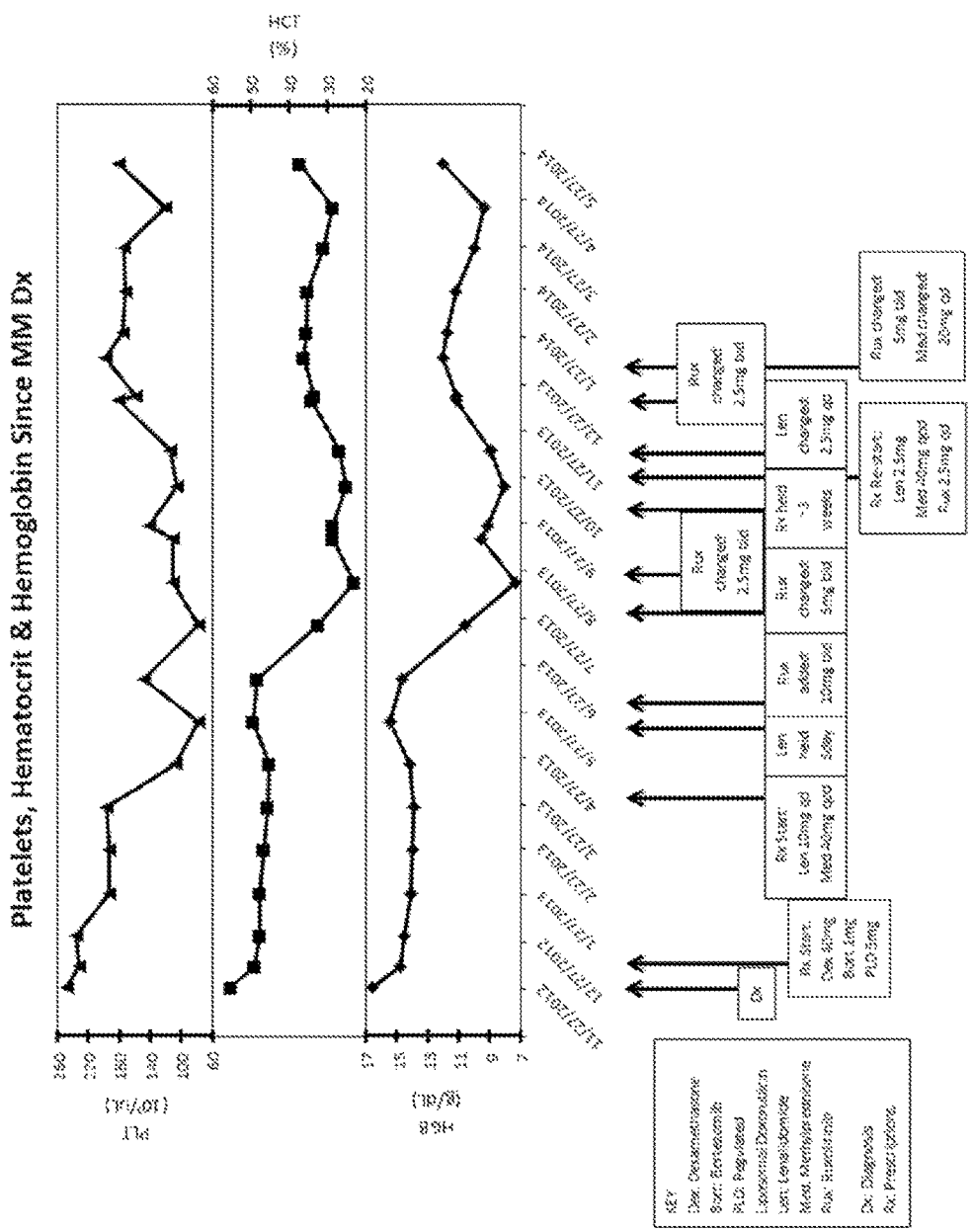
FIG. 10 shows a representative example of a patient's progress while undergoing treatments for multiple myeloma, including a combination of a JAK2 inhibitor, a thalidomide derivative, and a glucocorticoid. Measurements of platelets, hematocrit, and hemoglobin were taken from a patient beginning from the diagnosis of multiple myeloma. A graph shows measurements of platelets taken during treatment (top). A graph shows serum levels of hematocrit during the treatment (middle). A graph shows levels of hemoglobin during the treatment (bottom). Changes in medication during the treatment are indicated along the X-axis with arrows.
Figure 11:
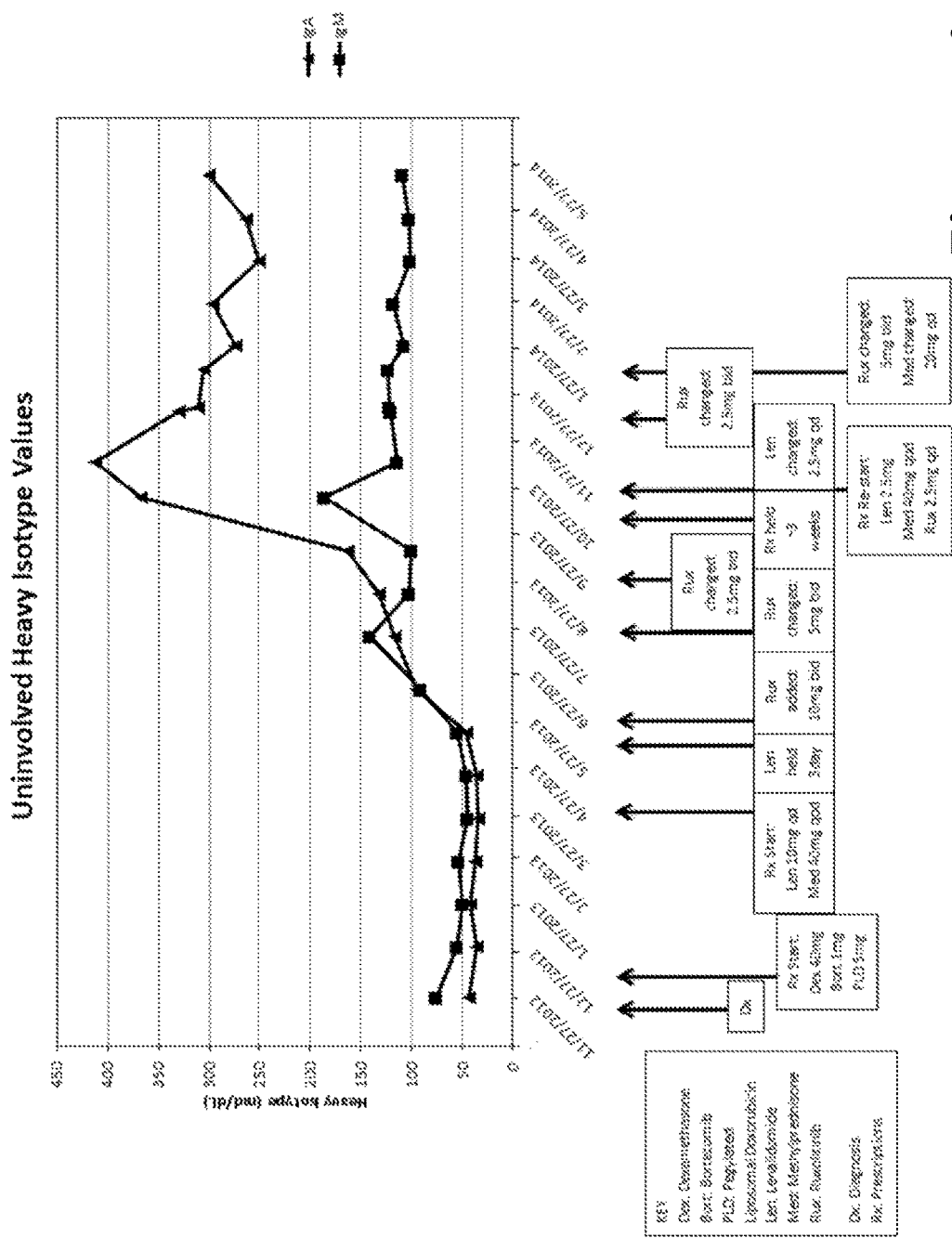
FIG. 11 shows a representative example of a patient's progress while undergoing different treatments for multiple myeloma, including a combination of a JAK2 inhibitor, a thalidomide derivative, and a glucocorticoid. Measurements of uninvolved heavy isotype levels were taken from a patient beginning with the diagnosis of multiple myeloma. A graph shows measurements of serum IgA and IgM levels during the treatment. Changes in medication during the treatment are indicated along the X-axis with arrows.

At the time of his diagnosis with multiple myeloma, the patient's labs results were: IgG: 5360 mg/dL, serum free light chain (SFLC): 1068 mg/L, serum M-Protein: 3.89 g/dL, and 24-hour urine M-Protein: 1413 mg. (FIGS. 9-11)

Treatment for multiple myeloma started on Dec. 11, 2012. The treatment included a chemotherapeutic agent, pegylated liposomal doxorubicin (PLD), a proteasome inhibitor, bortezomib and IV dexamethasone, a glucocorticoid. Monthly zoledronic acid treatment was started, and the previously administered ruxolitinib treatment the patient was undergoing for his PRV was discontinued. The lab results during this treatment were:

Dec. 31, 2012: Stable disease—IgG: 4410 mg/dL, SFLC: 1149.5 mg/L, and serum M-Protein: 3.35 g/dL Jan. 28, 2013: Stable disease—IgG: 4130 mg/dL, SFLC: 1328.7 mg/L, serum M-Protein: 3.26 g/dL, and 24-hour urine M-Protein: 1498 mg Feb. 25, 2013: Stable disease—IgG: 4090 mg/dL, SFLC: 1053.7 mg/L, serum M-protein: 3.12 g/dL, and 24-hour urine M-protein: 1306 mg Mar. 25, 2013: Progressive disease—IgG: 4620 mg/dL, serum M-Protein: 3.38 g/dL, and 24-hour urine M-protein: 1682 mg The PLD, bortezomib and dexamethasone combination was discontinued, and a new treatment regimen was started on Mar. 28, 2013. Lenalidomide (10 mg) was taken orally on days 1-21 of a 28 day treatment cycle, followed by 7 days (days 22-28) rest. The glucocorticoid methylprednisolone (40 mg) was taken orally every other day continuously. The lab results during this treatment were:

Apr. 22, 2013: Stable disease—IgG: 3680 mg/dL, SFLC: 451.6 mg/L, serum M-protein: 2.64 g/dL, and 24-hour urine M-protein: 740 mg May 17, 2013: WBC: 17.9, HGB: 16.3, HCT: 51.8, PLT: 84

The lenalidomide was held for 3 days secondary to right lower extremity acute deep vein thrombosis. The lab results during this treatment were:

May 20, 2013: Minimal Response—IgG: 2830 mg/dL, SFLC: 392.9 mg/L, serum M-protein: 2.45 g/dL, and 24-hour urine M-protein: 748 mg May 28, 2013: WBC: 24.3, HGB: 15.5, HCT: 50.1, PLT: 88

Ruxolitinib (10 mg, orally) was added twice daily on 5/28/13 to lenalidomide and methylprednisolone. The lab results during this treatment were:
Jun. 17, 2013: Minimal Response—IgG: 3160 mg/dL, SFLC: 204.1 mg/L, serum M-protein: 2.47 g/dL, and 24-hour urine M-protein: 550 mg
Jul. 22, 2013: Minimal Response—IgG: 2610 mg/dL, SFLC: 274.4 mg/L, serum M-protein: 2.23 g/dL, and 24-hour urine M-protein: 480 mg The ruxolitinib was reduced to 5 mg twice daily due to low blood counts. The lab results during this treatment were:
Aug. 19, 2013: Minimal Response—IgG: 2380 mg/dL, SFLC: 233.4 mg/L, serum M-protein: 1.91 g/dL, and 24-hour urine M-protein: 190 mg Ruxolitinib was reduced to 2.5 mg twice daily on 8/26/13 because of low blood counts. The lab results during this treatment were:
Sep. 16, 2013: Minimal Response—IgG: 2440 mg/dL, SFLC: 260.3 mg/L, serum M-protein: 1.99 g/dL, and 24-hour urine M-protein: 501 mg
Sep. 25, 2013: Minimal Response—24-hour urine M-protein: 379 mg
Oct. 21, 2013: Minimal Response—IgG: 2090 mg/dL, SFLC: 415.5 mg/L, and serum M-protein: 1.76 g/dL Zoledronic acid was held secondary to renal dysfunction. Lenalidomide, methylprednisolone and ruxolitinib were held from Oct. 8, 2013 to Oct. 27, 2013 secondary to hospitalization with *Staphylococcus aureus* sepsis and renal failure. The treatment was restarted on Oct. 28, 2013 with Lenalidomide at 2.5 mg every other day secondary to poor renal function, Methylprednisolone 40 mg every other day and Ruxolitinib 2.5 mg daily. Lenalidomide at 2.5 mg was changed to once daily on Nov. 11, 2013. Zoledronic acid continued to be held. The lab results during this treatment were:
Nov. 13, 2013: Minimal Response—IgG: 2170 mg/dL, SFLC: 250.2 mg/L, and serum M-protein: 1.83 g/dL
Dec. 16, 2013: Minimal Response—IgG: 2180 mg/dL, SFLC: 214.5 mg/L, and serum M-protein: 1.57 g/dL Ruxolitinib at 2.5 mg was changed to twice daily. The lab results during this treatment were:
Dec. 19, 2013: Minimal Response—IgG: 2150 mg/dL, SFLC: 210.9 mg/L, serum M-protein: 1.61 g/dL, and 24-hour urine M-protein: 249 mg
Jan. 13, 2014: Minimal Response—IgG: 2110 mg/dL, SFLC: 182.3 mg/L, and serum M-protein: 1.71 g/dL Ruxolitinib was increased to 5 mg twice daily on 1/13/14 and methylprednisolone
Jan. 29, 2014: Minimal Response—IgG: 2020 mg/dL, SFLC: 253.9 mg/L, serum M-protein: 1.51 g/dL, and 24-hour urine M-protein: 229 mg
Feb. 25, 2014: Minimal Response—IgG: 2040 mg/dL, SFLC 182.2 mg/L, serum M-protein: 1.58 g/dL, and 24-hour urine M-protein: 298 mg
Mar. 25, 2014: Minimal Response—IgG: 1820 mg/dL, SFLC: 197.5 mg/L, serum M-protein: 1.18 g/dL, and 24-hour urine M-protein: 327 mg
Apr. 21, 2014: Minimal Response—IgG: 1700 mg/dL, SFLC: 165.8 mg/L, and serum M-protein: 1.22 g/dL
May 20, 2014: Minimal Response—IgG: 1820 mg/dL, SFLC: 206.5 mg/L, serum M-protein: 1.30 g/dL, and 24-hour urine M-protein: 200 mg.

After adding ruxolitinib to his treatment with lenalidomide and methylprednisolone in late May 2013, the patient's myeloma labs showed and continue to show ongoing improvement:

| Laboratory test | May 2013 | May 2014 |
|---|---|---|
| IgG | 2830 mg/dL | 1820 mg/dL |
| Serum M-protein | 2.45 g/dL | 1.30 g/dL |
| SFLC | 392.9 mg/L | 206.5 mg/L |
| 24-hr urine M-protein | 748 mg | 200 mg |

In this case study, the patient exhibited sustained improvement while undergoing treatment for multiple myeloma that included the JAK2 inhibitor ruxolitinib, the thalidomide derivative lenalidomide, and the glucocorticoids, methylprednisone and methylprednisolone. During this combined treatment, the requirement for "minimal response" was consistently met with every lab result and the patient with further improvements recently has now approached "partial response" status. This study illustrates that the combination of a JAK2 inhibitor, thalidomide or a thalidomide derivative, and a glucocorticoid provides a much needed improved treatment regimen for patients undergoing treatments for hematological malignancies, including multiple myeloma.

Example 7

M2 Macrophage Polarization in Mm Patients Treated with a Jak2 Inhibitor

Macrophages are able to polarize into pro-inflammatory M1 or alternative M2 states with distinct phenotypes and physiological functions. M2 cells promote tumor growth and metastasis through secretion of growth factors. However, crosstalk between tumor cells and macrophages in the development of M2 macrophage polarization is not well understood. These experiments evaluate the proportion of M2 macrophages in bone marrow (BM) from patients (pts) with multiple myeloma (MM), the effects of MM cells on M2 and M1 differentiation in MM BM, and the effects of the JAK2 inhibitor ruxolitinib (RUX) on M2 polarization in MM.

The proportion of M1 and M2 macrophages in BM biopsies from MM pts with progressive disease and remission was determined using IFC analysis. The BM biopsy samples were stained with antibodies directed against human iNOS and CD86 for M1 and arginase 1(ARG1) and CD36 for M2 cells, following a standard IFC protocol. Monocytes/macrophage phenotype for M1 and M2 in mononuclear cells isolated from MM BM aspirate was also examined using flow cytometric analysis with these same antibodies. Human monocytes isolated from normal subjects or THP1 monocyte cell line were co cultured with MM cell lines or primary MM tumor cells with or without low concentrations (IC20) of ruxolitinib (RUX) using Transwell plates. The percentage of M1 and M2 macrophages was determined using flow cytometric analysis. Total RNA was extracted from monocytes followed the manufacturer's directions. Quantitative PCR assays were performed with TaqMan technology on a OneStepPlus instrument.

Figure 12:
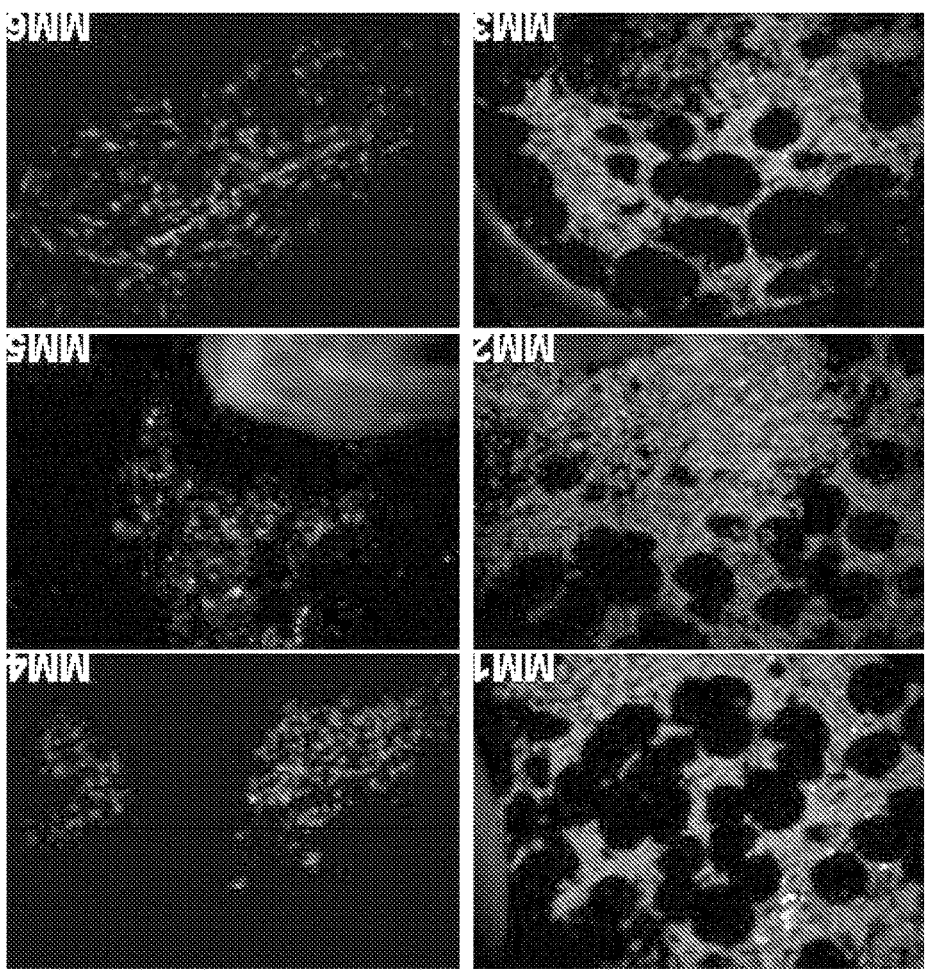
FIG. 12 shows the staining of CD36+(M2) macrophage cells in MMBM biopsies in treated patients. (A) Determination of CD36+(M2) macrophage cells of MMBM biopsy in MM patients by using a standard immunofluorescent (IFC) staining (20×). Left panel: Progressive disease; Right panel: Currently in remission. (B) Determination of CD36 (M2) macrophage cells of MMBM in MM patients by using a standard immunofluorescent (IFC) staining (40×). Left panel: Progressive disease; Right panel: Currently in remission.
Figure 12:
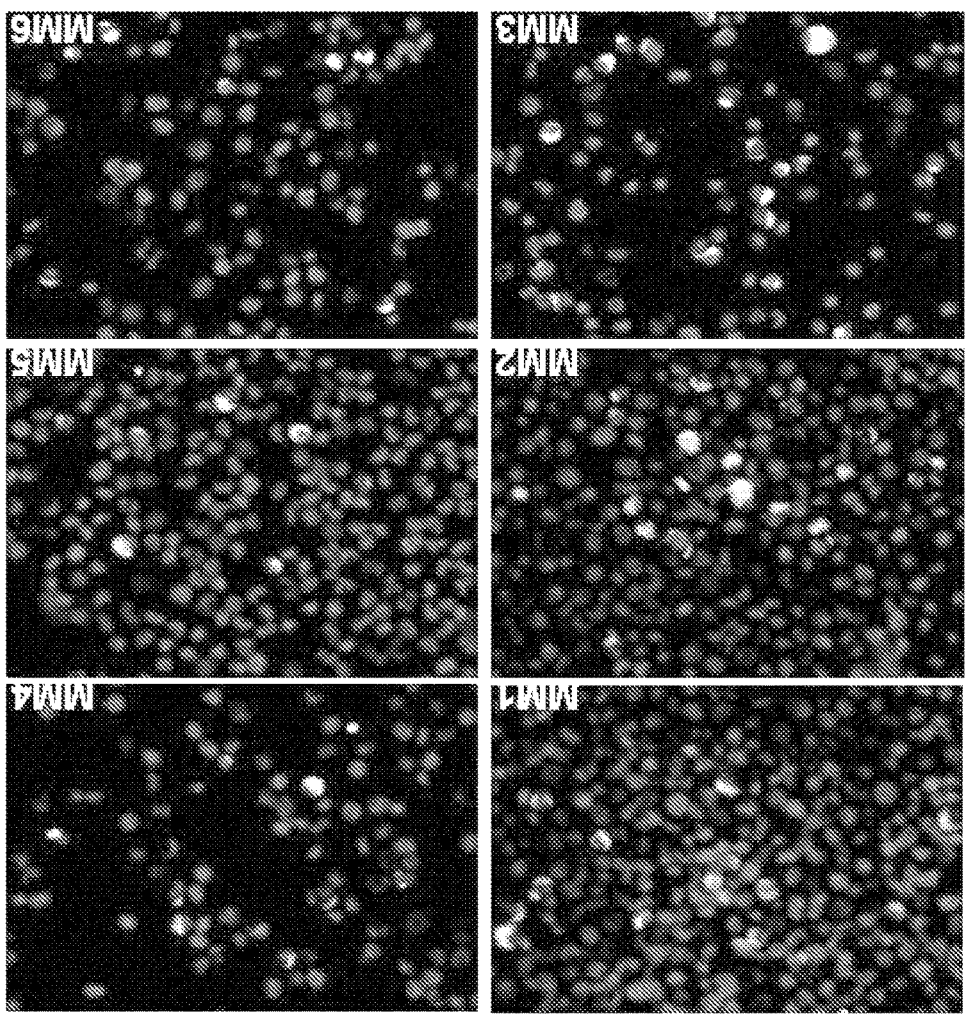
Figure 13:
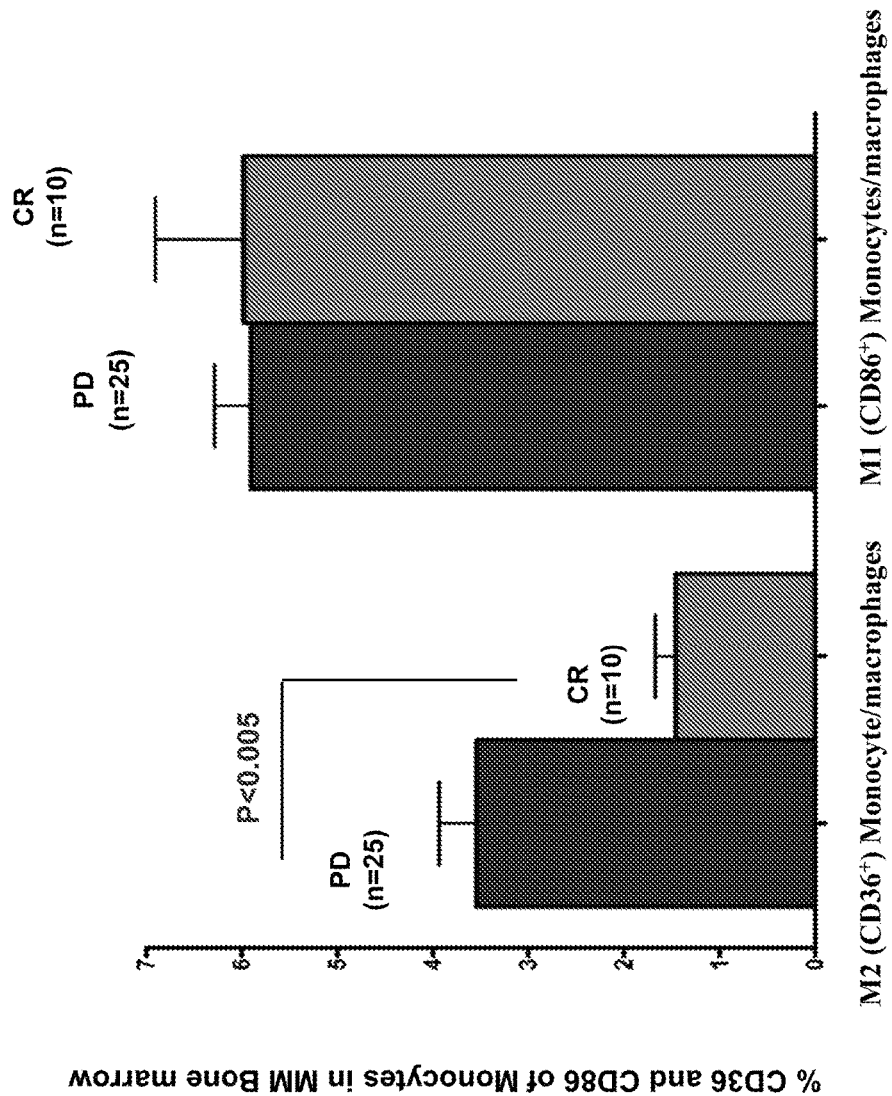
FIG. 13 shows the percentage of CD36+(M2)/monocytes in BM:M2 cells. (A) Percentage of M2 (CD36+) monocytes/macrophages in BM:M2 cells are significantly increased among MM patients with progressive disease (n=25) compared to those in complete remission (n=10) by flow cytometric analysis. M1(CD86+) macrophages are not changed. (B) Percentage of M2 (ARG1+) monocytes/macrophages in BM:M2 cells are significantly increased among MM patients with progressive disease (n=8) compared to those in complete remission (n=4) by flow cytometric analysis. M1 (iNOS+) monocytes/macrophages are significantly increased among MM patients with complete remission (n=4).
Figure 13:
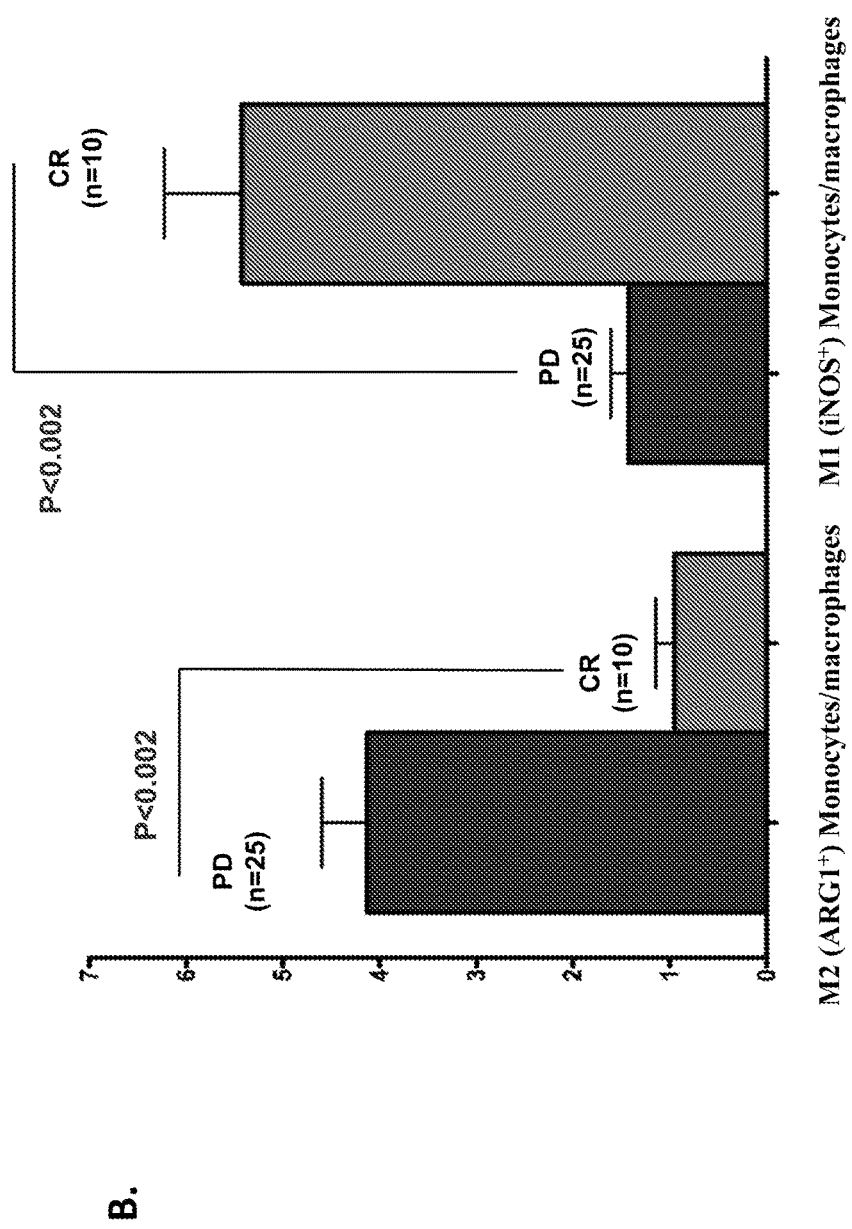
Figure 14:
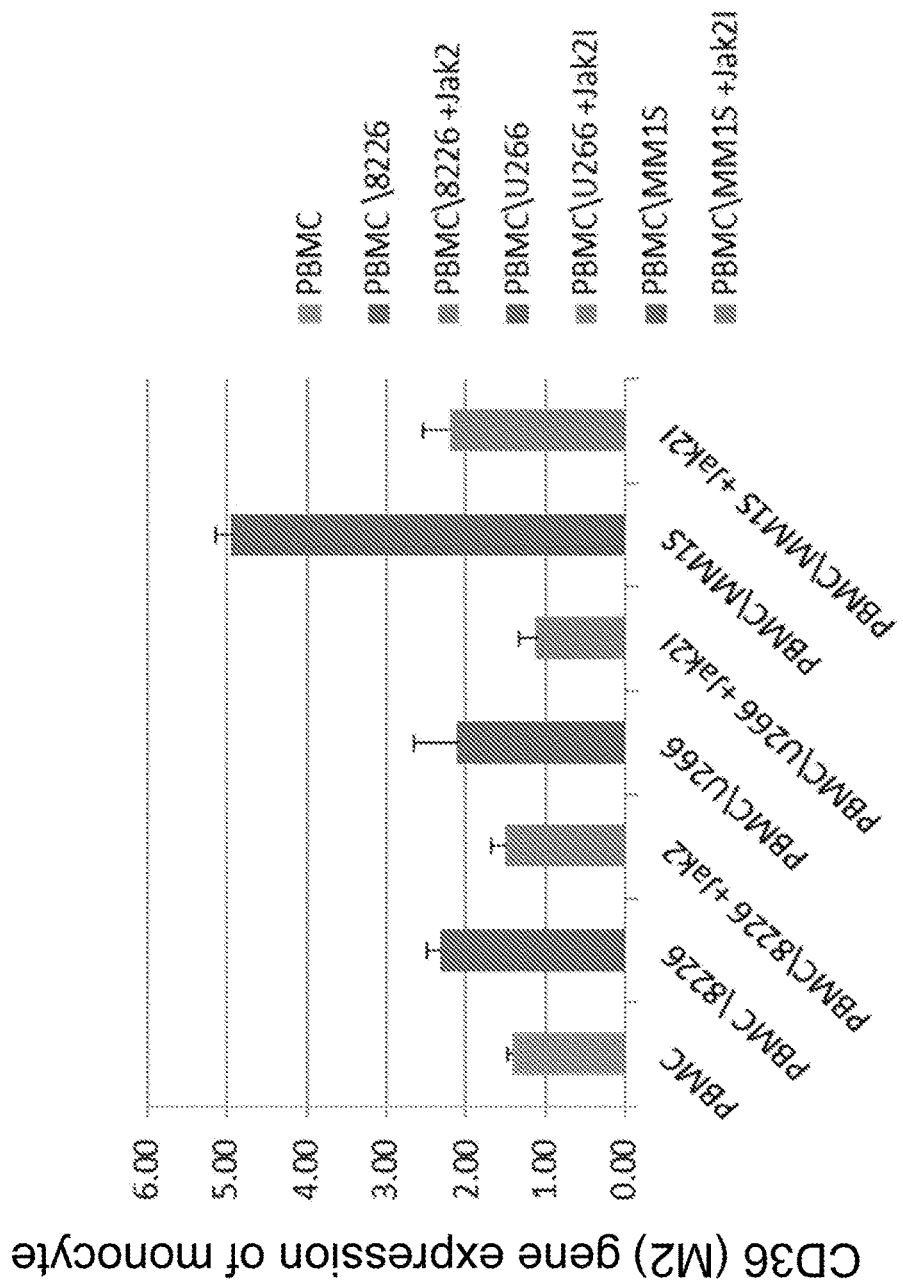
FIG. 14 shows that the gene expression of M2 monocytes (CD36+) was inhibited when monocytes co-cultured with MM tumor cells were treated with JAK2 inhibitor versus without JAK2 inhibitor.
Figure 15:
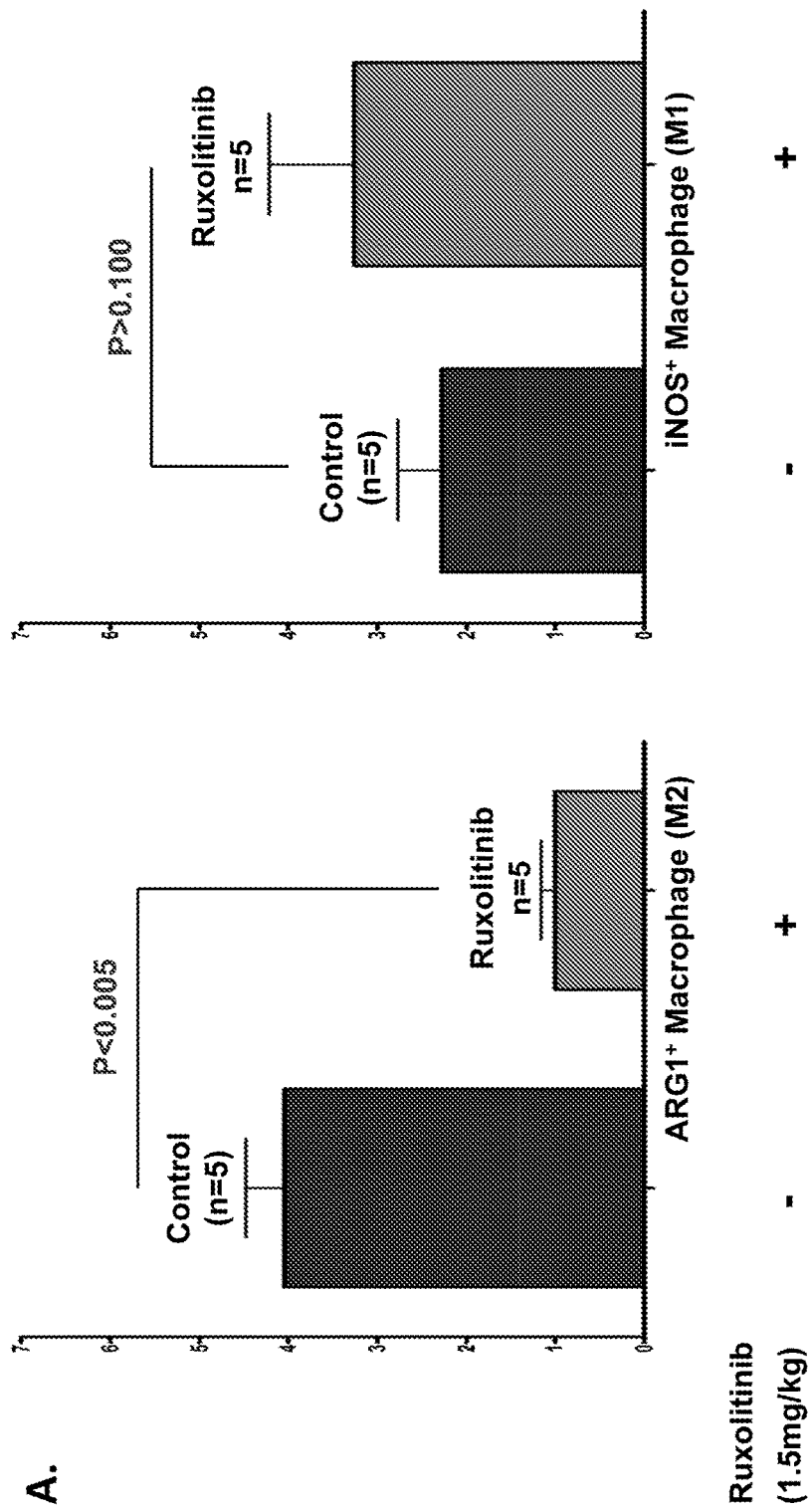
FIG. 15 shows the percentage of M2 (ARG1+) macrophages in a LAGκ2 MM animal model. (A) The percentage of M2 (ARG1+) macrophages in LAGκ2 MM animal model: M2 cells are significantly decreased in LAGκ2 MM animal model treated with JAK2 inhibitor, Ruxolitinib (1.5 mg/kg) (n=5) compared to untreated group (n=5) (Left panel). The percentage of M1 (iNOS+) macrophages is not changed (Right panel). The macrophages were analyzed by flow cytometric analysis. (B) The percentage of M2 (CD36+) macrophages in LAGκ2 MM animal model: M2 cells are significantly decreased in LAGκ2 MM animal model treated with JAK2 inhibitor, Ruxolitinib (1.5 mg/kg) (n=5) compared to untreated group (n=5) (Left panel). The percentage of M1 (CD86+) macrophages is not changed (Right panel). The macrophages were analyzed by flow cytometric analysis.
Figure 15:
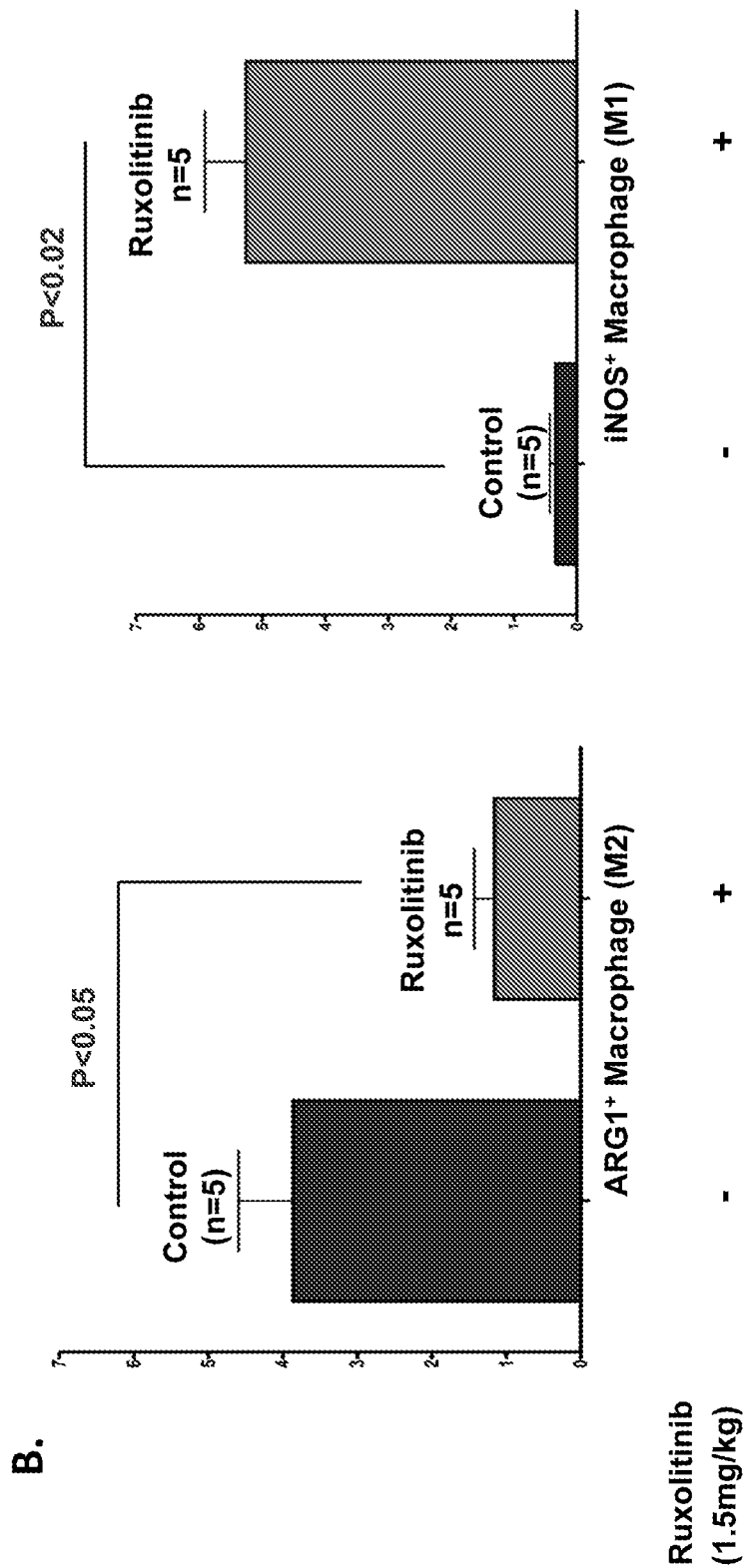

IHC demonstrated that the percentage of M2 macrophages (CD36+/ARG1+) was markedly increased in BM sections from MM pts with progressive disease compared with those pts in remission (FIG. 12A, 12B). The flow cytometric data also showed the percentage of M2 (CD36+/ARG1+) macrophages in BM was significantly increased in MM patients with progressive disease (n=20) compared to those in remission (n=9; P=0.005) whereas there was no significant difference in the percentage of M1 (CD86+/iNOS+) macrophages in BM derived from MM patients with progressive disease compared to those in remission (FIG. 13A, 13B). The results of Quantitation PCR showed CD36 gene expression was reduced by JAK2 inhibitor in monocytes co-cultured with all three MM cell lines: RPMI1640, U266, and MM1s (FIG. 14). Moreover, when direct cell-to-cell contact occurred between the MM cells and the monocytes, the percentage of M2 macrophages markedly increased after 7 days of incubation. The percentage of M2 (ARG1+) macrophages was significantly decreased in LAGκ2 MM animal model (n=5) treated with JAK2 inhibitor, Ruxolitinib (1.5 mg/kg) compared to the untreated group (n=5) (FIG. 15A). The percentage of M1 (iNOS+) macrophages was not changed (FIG. 15A) when assayed by flow cytometric analysis. The percentage of M2 (CD36+) macrophages was markedly decreased in LAGκ2 MM animal model (n=5) treated with JAK2 inhibitor, Ruxolitinib (1.5 mg/kg) compared to the untreated group (FIG. 15B). The percentage of M1 (CD86+) macrophages was increased (FIG. 15B) when assayed by flow cytometric analysis.

These results show that MM tumor cells induced monocytes polarization to M2 macrophages and promoted tumor cell growth. M2 cells were present at high numbers in BM derived from MM patients with progressive disease. The JAK 2 inhibitor RUX significantly decreased M2 macrophage polarization and tumor growth in MM.

Example 8

Materials and Methods

Cells, Cell Lines, Cell Culture, and Collection of Multiple Myeloma Bone Marrow Mononuclear Cells Bone marrow aspirates were collected from multiple myeloma patients after obtaining Institutional Review Board approval (Western IRB BIO 001), and informed consent was obtained in accordance with the Declaration of Helsinki Bone marrow mononuclear cells (BMMCs) were isolated using density-gradient centrifugation using Histopaque-1077 (Sigma-Aldrich, St Louis, Mo.). The human multiple myeloma cell lines RPMI8226 and U266 were obtained from American Type Culture Collection (Rockville, Md., USA). The MM1s multiple myeloma cell line was provided by Dr. Steven Rosen (Northwestern University, Chicago, Ill., USA). The cell lines and BMMCs were maintained in RPMI 1640 (Omega Scientific, Tarzana, Calif., USA) supplemented with 10% fetal bovine serum, 2 mmol/11-glutamine, and essential amino acids in an atmosphere of 5% carbon dioxide at 37° C.

Cell Proliferation MTS Assay

Cells were seeded at $10^5$ cells per well in 96-well plates and incubated for 24 h. The tumor cells were cultured in the presence of vehicle, JAK2 inhibitor (ruxolitinib or tofacitinib), lenalidomide, dexamethasone, or two-drug combinations: ruxolitinib+lenalidomide, ruxolitinib+dexamethasone, or tofacitinib+lenalidomide or tofacitinib+dexamethasone, or three-drug combinations; ruxolitinib+lenalidomide+dexamethasone or tofacitinib+lenalidomide+dexamethasone for 48 h. After the incubation period, cell viability was quantified using the CellTiter 96 well Queous Non-Radioactive Cell Proliferation Assay (Promega, Madison, Wis., USA). Each well was treated with MTS (3-(4,5-dimethylthiazol-2-yl)-5-(3-carboxymethoxyphenyl)-2-(4-sulfophenyl)-2H-tetrazolium, inner salt) for 1-4 h, after which absorbance was recorded at 490 nm. The quantity of formazan product as measured by absorbance at 490 nm is directly proportional to the number of living cells in culture. In vitro synergy between JAK2 inhibitors and ruxolitinib or tofacitinib was assessed using the median effect method of Chou and Talalay (Chou & Talalay, 1984). Combination indices (CIs) were calculated separately for each combination.

Generation of Severe Combined Immunodeficient Mice Containing Human Myeloma Tumors Six- to 8-week-old male severe combined immunodeficient (SCID) mice were obtained from the Jackson Laboratory (Bar Harbor, Me., USA) and maintained in a specific pathogen-free area in our animal resources facility. Human myeloma tumors (LAGκ-1A or LAGκ-2) which have been maintained in our laboratory for many years were excised from an anaesthetized tumor containing donor mouse, sectioned into 20-40 mm3 pieces, and surgically implanted into the left superficial gluteal muscle of the anaesthetized naive SCID mice. Recipient mice received weekly injections of anti-asialo GM1 rabbit serum (Wako Bioproducts, Richmond, Va., USA) to further suppress immune activity and allow growth of the human tumor. All animal studies were conducted according to protocols approved by the Institutional Animal Care and Use Committee. Animals were anaesthetized with ketamine, xylazine, and isoflurane prior to surgery and were euthanized when tumors reached 2 cm in diameter.

In Vivo Study Treatment

Mice containing one of the human multiple myeloma xenografts were blindly assigned to one of the experimental groups, and treatment was initiated 7-21 d after tumor implantation. Ruxolitinib was administered via intraperitoneal injection at 1.5 mg/kg, twice daily. Dexamethasone was administered at 1 mg/kg, once daily via intraperitoneal injection. Lenalidomide was administered via oral gavage at 15 mg/kg, once daily. As a direct measurement of tumor growth, calipers were used to assess tumor volume weekly, and the formula for an ellipsoid volume was applied ($4/3 \pi \times [width/2]2 \times [length/2]$). Percentage inhibition of tumor growth was represented as the tumor volume of the test drug group over the tumor volume of the untreated group (T/C). The optimal value is the minimal T/C ratio that reflects the maximal tumor growth inhibition achieved. The criterion for efficacy for the T/C ratio was <42%, according to National Cancer Institute (NCI) standard criteria (Bissery et al, 1991).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating multiple myeloma in a subject comprising administering to the subject ruxolitinib, lenalidomide and a glucocorticoid, wherein the glucocorticoid is selected from the group consisting of dexamethasone, methylprednisolone, methylprednisone and prednisone.

2. The method of claim 1, comprising administering ruxolitinib orally.

3. The method of claim 1, comprising administering ruxolitinib at a dose of 1-50 mg.

4. The method of claim 1, comprising administering lenalidomide orally.

5. The method of claim 1, comprising administering lenalidomide at a dose of 1-50 mg.

6. The method of claim 1, comprising administering dexamethasone intravenously.

7. The method of claim 1, comprising administering dexamethasone orally.

8. The method of claim 1, comprising administering dexamethasone at a dose of 1-100 mg.

9. The method of claim 1, comprising administering methylprednisolone, methylprednisone or prednisone orally.

10. The method of claim 1, comprising administering methylprednisolone, methylprednisone or prednisone at a dose of 1-100 mg.

11. A method of treating relapsed or refractory multiple myeloma in a subject comprising administering to the subject ruxolitinib, lenalidomide, and a glucocorticoid, wherein the glucocorticoid is selected from the group consisting of dexamethasone, methylprednisolone, methylprednisone and prednisone.

12. A method of treating relapsed multiple myeloma in a subject comprising administering to the subject, ruxolitinib, lenalidomide, and a glucocorticoid, wherein the glucocorticoid is selected from the group consisting of dexamethasone, methylprednisolone, methylprednisone and prednisone.

13. A method of treating multiple myeloma that is refractory to prior treatment for multiple myeloma comprising administering to a subject, ruxolitinib, lenalidomide, and a glucocorticoid, wherein the glucocorticoid is selected from the group consisting of dexamethasone, methylprednisolone, methylprednisone and prednisone.

14. The method of claim 13, wherein the prior treatment comprises administration of thalidomide or a derivative thereof and a glucocorticoid; wherein the thalidomide or a derivative thereof is selected from the group consisting of thalidomide, lenalidomide, pomalidomide, linomide, CC-1088, CDC-501, and CDC-801.

15. The method of claim 13, wherein the prior treatment comprises administration of thalidomide, lenalidomide, pomalidomide, linomide, CC-1088 CDC-501 or CDC-801.

16. The method of claim 13, wherein the prior treatment comprises administration of a proteasome inhibitor.

17. The method of claim 1, wherein the subject has received at least one to three previous treatments for multiple myeloma.

18. The method of claim 17, the subject was previously treated with a chemotherapeutic agent.

19. The method of claim 17, wherein the subject was previously treated with doxorubicin, melphalan, etoposide, cytarabine, and bendamustine.

20. The method of claim 17, the subject was previously treated with a proteasome inhibitor.

21. The method of claim 17, the subject was previously treated with bortezomib.

22. The method of claim 17, wherein the subject was previously treated with thalidomide, lenalidomide, pomalidomide, linomide, CC-1088, CDC-501, or CDC-801.

23. The method of claim 17, the subject was previously treated with a glucocorticoid.

24. The method of claim 17, wherein the subject was previously treated with thalidomide or a derivative thereof, and a glucocorticoid; wherein the thalidomide or a derivative thereof is selected from the group consisting of thalidomide, lenalidomide, pomalidomide, linomide, CC-1088, CDC-501, and CDC-801.

* * * * *